United States Patent
Tachas et al.

(10) Patent No.: US 11,041,156 B2
(45) Date of Patent: Jun. 22, 2021

(54) MOBILIZING LEUKEMIA CELLS

(71) Applicants: Antisense Therapeutics Ltd, Toorak (AU); Children's Hospital of Los Angeles, Los Angeles, CA (US)

(72) Inventors: George Tachas, Kew (AU); Yong-Mi Kim, Los Angeles, CA (US)

(73) Assignees: Antisense Therapeutics Ltd, Toorak (AU); Children's Hospital of Los Angeles, Los Angeles, CA (US)

( * ) Notice: Subject to any disclaimer, the term of this patent is extended or adjusted under 35 U.S.C. 154(b) by 0 days.

(21) Appl. No.: 15/971,938

(22) Filed: May 4, 2018

(65) Prior Publication Data

US 2018/0355360 A1  Dec. 13, 2018

Related U.S. Application Data

(63) Continuation-in-part of application No. PCT/AU2016/051059, filed on Nov. 4, 2016.

(30) Foreign Application Priority Data

Nov. 5, 2015  (AU) .................. 2015904547

(51) Int. Cl.
| | |
|---|---|
| *C07H 21/04* | (2006.01) |
| *C12N 15/113* | (2010.01) |
| *A61K 31/7125* | (2006.01) |
| *A61K 45/06* | (2006.01) |
| *A61P 35/02* | (2006.01) |
| *A61K 31/7076* | (2006.01) |

(52) U.S. Cl.
CPC ...... *C12N 15/1138* (2013.01); *A61K 31/7076* (2013.01); *A61K 31/7125* (2013.01); *A61K 45/06* (2013.01); *A61P 35/02* (2018.01); *C12N 2310/11* (2013.01); *C12N 2310/321* (2013.01); *C12N 2310/322* (2013.01); *C12N 2310/3341* (2013.01); *C12N 2310/341* (2013.01); *C12N 2310/346* (2013.01); *C12N 2320/30* (2013.01)

(58) Field of Classification Search
None
See application file for complete search history.

(56) References Cited

U.S. PATENT DOCUMENTS 6,258,790 B1 * 7/2001 Bennett .................. A61P 11/06
514/44 A

FOREIGN PATENT DOCUMENTS

| WO | WO 2000/020635 A1 | 4/2000 |
|---|---|---|
| WO | WO 2000/039292 A2 | 7/2000 |
| WO | WO 2006/086821 A1 | 8/2006 |
| WO | WO 2012/034194 A1 | 3/2012 |

OTHER PUBLICATIONS

Antisense Therapeutics, ANZCTR [online], Feb. 25, 2014, ACTRN12614000200684, "A Phase I, Randomised, Open Label Study to Assess the Safety, Tolerability, Pharmacokinetics and Pharmacodynamics of Subcutaneous Doses of ATL1102 Alone and in combination with G-CSF in Healthy Volunteers" [retrieved online Nov. 18, 2016] <URL: https://www.anzctr.org.au/Trial/Registration/TrialReview.aspx?id=365339&isReview=true>.
Limmroth C. et al.:"CD49d antisense drug ATL1102 reduces disease activity in patients with relapsing-remitting MS" *Neurology*, 2014, vol. 83, No. 20, pp. 1780-1788.
Duchartre Y. et al.: "A Novel CD49d Targeting Antisense, ATL1102, Effectively Mobilizes Acute Myeloid Leukemia Cells" *Blood*, Dec. 3, 2015, vol. 126, pp. 3807 [retrieved online Nov. 18, 2016] <URL: http://www.bloodjournal.org/content/126/23/3807>.
International Search Report and Written Opinion for International Application No. PCT/AU2016/051059, dated Nov. 24, 2016.
Extended European Search Report dated Mar. 20, 2019 issued in European Patent Application No. 16861126.7.
Examination Report dated Jun. 19, 2020 issued in European Patent Application No. 16861126.7.
Kronenwett R et al: "Functional analyses of antisense oligonucleotide-mediated downregulation of the integrin VLA-4 in normal and leukemic hematopoietic cells", Blood, vol. 92, No. 10 Suppl. 1 Part 1-2, Nov. 15, 1998, p. 586A.

* cited by examiner

*Primary Examiner* — Kimberly Chong
(74) *Attorney, Agent, or Firm* — Knobbe, Martens, Olson & Bear, LLP

(57) ABSTRACT

A method for mobilizing leukemia cells which are α4 integrin positive to the peripheral blood of a human subject, the method comprising administering to the human subject an effective amount of an antisense compound to α4 integrin. The cells may be mobilized from bone marrow. The antisense compound is: 5'-$^{Me}C^{Me}C$UG AGT $^{Me}$CTG TTT $^{Me}U^{Me}C^{Me}CA^{Me}U^{Me}U$ $^{Me}C^{Me}$U-3' wherein, (a) each of the 19 internucleotide linkages of the oligonucleotide is an O,O-linked phosphorothioate diester; (b) the nucleotides at the positions 1 to 3 from the 5' end are 2'-O-(2-methoxyethyl) modified ribonucleosides; (c) the nucleotides at the positions 4 to 12 from the 5' end are 2'-deoxyribonucleosides; (d) the nucleotides at the positions 13 to 20 from the 5' end are 2'-O-(2-methoxyethyl) modified ribonucleosides; and (e) all cytosines are 5-methylcytosines ($^{Me}C$), or a pharmaceutically acceptable salt thereof.

16 Claims, 20 Drawing Sheets
Specification includes a Sequence Listing.

A

B

C

D

A

Experiment to determine ATL1102+Arac survival in vivo

A

| U937 luc | Treatment Regimen | | | | | | | | | | | | | |
|---|---|---|---|---|---|---|---|---|---|---|---|---|---|---|
| Ara-c 100~300mg/kg | ▼ | ▼ | ▼ | ▼ | ▼ | ▼ | | | | ▼ | ▼ ▼ | ▼ ▼ | ▼ ▼ | ▼ |
| ATL1102 or Antisense ctrl 150mg/kg | | | ▼ | | | | ▼ | | | | | | | | |
| | 3 | 5 | 7 | | | 11 | 13 | 15 | | 18 | 20 22 | 25 27 | 31 | | |

U937 luc: 0.05x10^6 cells/NSG female mouse
Ara-c: 100mg/kg 3 times/week for first 5 times Tx and 300mg/kg thereafter weeks.
ATL1102 or Antisense ctrl: 150mg/kg/time, once a week for first 2 weeks followed by 3 times/week.

Fig. 8A

Weight changes including Dm03, receiving the 2nd cycle of treatment

A

B

MOBILIZING LEUKEMIA CELLS

CROSS-REFERENCE TO RELATED APPLICATIONS

This application is a continuation-in-part of International Application No. PCT/AU2016/051059, filed Nov. 4, 2016, which claims priority to Australian Patent Application No. 2015904547, filed Nov. 5, 2015, each of which is hereby incorporated by reference in its entirety into this application.

TECHNICAL FIELD

The present disclosure provides methods for the mobilization of leukemia cells. In one example, the present disclosure provides methods for the mobilization of leukemia cells from the bone marrow to the peripheral blood. The present invention also provides methods of treatment of leukemia, for example, acute myeloid leukemia (AML).

BACKGROUND

Leukemia is a cancer of the early blood-forming cells, and is often described as being either acute (fast growing) or chronic (slow growing). Acute leukemia is a clonal expansion of tumoral cells in bone marrow, blood or other tissues. The acute leukemias are classified as myeloid or lymphoid based on the lineage of the blast cells (Camos et al., Clinical Translational Oncology 8 (8):550-9, 2006). Acute lymphoblastic leukemia (ALL) is a haematological disorder with a survival rate of 40% in adults and 80-90% in children (Hunger et al., New England Journal of Medicine 15; 373(16):1541-52, 2015). AML is also a hematological disorder, with poor five year overall survival (less than 30%), owing to a high relapse rate Schlenk et al. New England Journal of Medicine 2008; 358:1909-1918; Döhner et al., New England Journal of Medicine 15 2015 Sep. 17; 373 (12):1136-52). There are about 54,270 leukemia cases a year in the United States, with about 6,250 cases of ALL, 20,830 cases of AML, 14,620 cases of CLL, 6660 cases of CML and 5,910 cases of other leukemias per year (Cancer.org: American Cancer Society 2014). The bone marrow (BM) microenvironment including the endosteal, vascular and stromal niche, has been shown to be the most frequent site of relapse of leukemia (Gaynon et al. Cancer 1998; 82:1387-1395).

Treatment is dominated by generic chemotherapeutic agents, predominantly cytarabine and daunorubicin (What's new in acute myeloid leukemia research and treatment? American Cancer Society (2014)). Therapy for AML includes remission induction followed by postremission chemotherapy for most patients. For some, this is followed by hematopoietic stem cell transplantation (HSCT). Treatment recommendations for AML vary, taking into account patient age, cytogenetics, and prognostic factors.

There is a strong focus on the introduction of targeted therapy, with a wide range of novel targets specific to AML, growth and progression under development. These are predominately Small Molecule (SM) inhibitors of serine threonine protein kinases, immunological agents against tumor associated antigens/genes, and antagonists against cell-surface receptors.

Novel strategies to maximise remission rates in response to treatment and to prolong remission duration are clearly needed.

SUMMARY

Accordingly, in one embodiment, the present disclosure provides a method for mobilizing leukemia cells which are α4 integrin positive to the peripheral blood of a human subject. In one embodiment, the method comprises administering to the human subject an effective amount of an antisense compound to α4 integrin. In some embodiments, the leukemia cells are mobilized from the bone marrow.

In one embodiment, the antisense compound is:

(SEQ ID NO: 1)

wherein, a) each of the 19 internucleotide linkages of the oligonucleotide is an O,O-linked phosphorothioate diester;
b) the nucleotides at the positions 1 to 3 from the 5' end are 2'-O-(2-methoxyethyl) modified ribonucleosides;
c) the nucleotides at the positions 4 to 12 from the 5' end are 2'-deoxyribonucleosides;
d) the nucleotides at the positions 13 to 20 from the 5' end are 2'-O-(2-methoxyethyl) modified ribonucleosides; and
e) all cytosines are 5-methylcytosines ($^{Me}C$),
or a pharmaceutically acceptable salt thereof.

Illustrative antisense compounds are described by sequence in SEQ ID NO: 1 (human α4 integrin antisense sequence) and SEQ ID NO:2 (mouse α4 integrin antisense sequence).

In one embodiment, the leukemia cells are neutrophilic and/or monocytic leukemia cells.

In one embodiment, the present description enables a method for mobilizing leukemia cells to the peripheral blood of a subject, the method comprising administering to the subject an effective amount of antisense compound:

(SEQ ID NO: 1)

wherein, a) each of the 19 internucleotide linkages of the oligonucleotide is an O,O-linked phosphorothioate diester;
b) the nucleotides at the positions 1 to 3 from the 5' end are 2'-O-(2-methoxyethyl) modified ribonucleosides;
c) the nucleotides at the positions 4 to 12 from the 5' end are 2'-deoxyribonucleosides;
d) the nucleotides at the positions 13 to 20 from the 5' end are 2'-O-(2-methoxyethyl) modified ribonucleosides; and
e) all cytosines are 5-methylcytosines (MeC),
or a pharmaceutically acceptable salt thereof.

In one embodiment, the leukemia cells are mobilized from the bone marrow.

In one embodiment, the leukemia cells are CD34+ and/or CD33+ cells.

In another embodiment, the leukemia is AML.

In one embodiment, the leukemia cells are CD123+, CD34+ and CD38−.

In one embodiment, the above described methods further comprise administering an additional α4 integrin antagonist prior to, subsequently, or concurrently with the antisense compound.

In one embodiment, the above described methods further comprise administering a therapeutic agent prior to, subsequently, or concurrently with the antisense compound.

In one embodiment, the therapeutic agent is a chemotherapeutic agent or an immune-oncolytic agent.

In one embodiment, the therapeutic agent is administered about 24 hours after administration of the antisense compound.

In one embodiment, the method further comprises monitoring the number of leukemia cells in the peripheral blood prior administering the therapeutic agent. In one embodiment, leukemia cells are monitored by flow cytometry. Other approaches are known in the art.

In one embodiment, leukemia cells are monitored for expression of one or more cell surface antigenic determinants.

In one embodiment, leukemia cells are monitored for expression of one or more cell surface antigenic determinants selected from CD33, CD123, CD34 and CD38.

In another approach, the present description enables a method for the treatment of leukemia in a human subject, said method comprising administering to the subject an effective amount of an antisense compound to α4 integrin.

In one embodiment, the method comprises administering to the subject an effective amount of antisense compound having the structure:

(SEQ ID NO: 1)

wherein,
a) each of the 19 internucleotide linkages of the oligonucleotide is an O,O-linked phosphorothioate diester;
b) the nucleotides at the positions 1 to 3 from the 5' end are 2'-O-(2-methoxyethyl) modified ribonucleosides;
c) the nucleotides at the positions 4 to 12 from the 5' end are 2'-deoxyribonucleosides;
d) the nucleotides at the positions 13 to 20 from the 5' end are 2'-O-(2-methoxyethyl) modified ribonucleosides; and
e) all cytosines are 5-methylcytosines (MeC),
or a pharmaceutically acceptable salt thereof, wherein the antisense compound inhibits the expression of α4 integrin.

In yet another approach, the present specification contemplates a method for the treatment of leukemia in a human subject, said method comprising;
(i) administering to the subject an effective amount of an antisense compound to α4 integrin; and
(ii) administering to the subject a therapeutic agent prior to, subsequently, or concurrently with the antisense compound.

In some embodiments, the method comprises administering to the subject an effective amount of antisense compound to α4 integrin having the structure:

(SEQ ID NO: 1)

wherein,
a) each of the 19 internucleotide linkages of the oligonucleotide is an O,O-linked phosphorothioate diester;
b) the nucleotides at the positions 1 to 3 from the 5' end are 2'-O-(2-methoxyethyl) modified ribonucleosides;
c) the nucleotides at the positions 4 to 12 from the 5' end are 2'-deoxyribonucleosides;
d) the nucleotides at the positions 13 to 20 from the 5' end are 2'-O-(2-methoxyethyl) modified ribonucleosides; and
e) all cytosines are 5-methylcytosines (MeC),
or a pharmaceutically acceptable salt thereof.

In one embodiment, the therapeutic agent is a chemotherapeutic agent.

In one embodiment, the method further comprises monitoring the number of leukemia cells in the peripheral blood prior to administering the therapeutic agent.

In one embodiment, leukemia cells are monitored for expression of one or more cell surface antigenic determinants selected from CD33, CD123, CD34 and CD38.

In one embodiment, the method further comprises administering an additional α4 integrin antagonist prior to, subsequently, or concurrently with the antisense compound.

In one embodiment, the method further comprises administering a therapeutic agent prior to, subsequently, or concurrently with the antisense compound.

In one embodiment, the therapeutic agent is a chemotherapeutic agent.

In one non-limiting embodiment, the therapeutic agent is administered about 24 hours after administration of the antisense compound.

In one embodiment, the method further comprises monitoring the number of leukemia cells in the peripheral blood prior administering the therapeutic agent.

In one embodiment, the leukemia cells are monitored by flow cytometry.

In one embodiment, the leukemia cells are monitored for expression of one or more cell surface antigenic determinant, selected from CD123, CD34 and CD38.

In another approach the present description enables the use of an antisense compound to α4 integrin as follows:

(SEQ ID NO: 1)

wherein,
a) each of the 19 internucleotide linkages of the oligonucleotide is an O,O-linked phosphorothioate diester;
b) the nucleotides at the positions 1 to 3 from the 5' end are 2'-O-(2-methoxyethyl) modified ribonucleosides;
c) the nucleotides at the positions 4 to 12 from the 5' end are 2'-deoxyribonucleosides;
d) the nucleotides at the positions 13 to 20 from the 5' end are 2'-O-(2-methoxyethyl) modified ribonucleosides; and
e) all cytosines are 5-methylcytosines (MeC),
or a pharmaceutically acceptable salt thereof.
for the manufacture of a preparation for the treatment of leukemia.

Thus, the specification provides of an antisense compound to α4 integrin for use or when used in the treatment of leukemia, wherein the antisense compound is

(SEQ ID NO: 1)

wherein,
a) each of the 19 internucleotide linkages of the oligonucleotide is an O,O-linked phosphorothioate diester;
b) the nucleotides at the positions 1 to 3 from the 5' end are 2'-O-(2-methoxyethyl) modified ribonucleosides;
c) the nucleotides at the positions 4 to 12 from the 5' end are 2'-deoxyribonucleosides;
d) the nucleotides at the positions 13 to 20 from the 5' end are 2'-O-(2-methoxyethyl) modified ribonucleosides; and
e) all cytosines are 5-methylcytosines (MeC),
or a pharmaceutically acceptable salt thereof.

In another approach, the present description enables the use of an antisense compound to α4 integrin:

(SEQ ID NO: 1)

wherein,
a) each of the 19 internucleotide linkages of the oligonucleotide is an O,O-linked phosphorothioate diester;
b) the nucleotides at the positions 1 to 3 from the 5' end are 2'-O-(2-methoxyethyl) modified ribonucleosides;
c) the nucleotides at the positions 4 to 12 from the 5' end are 2'-deoxyribonucleosides;
d) the nucleotides at the positions 13 to 20 from the 5' end are 2'-O-(2-methoxyethyl) modified ribonucleosides; and
e) all cytosines are 5-methylcytosines (MeC),
or a pharmaceutically acceptable salt thereof.
for the manufacture of a preparation for the treatment of AML.

Thus, the specification provides of an antisense compound to α4 integrin:

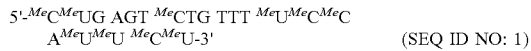

(SEQ ID NO: 1)

wherein,
a) each of the 19 internucleotide linkages of the oligonucleotide is an O,O-linked phosphorothioate diester;
b) the nucleotides at the positions 1 to 3 from the 5' end are 2'-O-(2-methoxyethyl) modified ribonucleosides;
c) the nucleotides at the positions 4 to 12 from the 5' end are 2'-deoxyribonucleosides;
d) the nucleotides at the positions 13 to 20 from the 5' end are 2'-O-(2-methoxyethyl) modified ribonucleosides; and
e) all cytosines are 5-methylcytosines (MeC),
or a pharmaceutically acceptable salt thereof.
for use or when used in the treatment of AML.

BRIEF DESCRIPTION OF DRAWINGS

(FIG. 2A) The percentage of CD49d positive cells with surface expression of CD49d are measured. (FIG. 2B) The PE mean of fluorescence are measured.

(FIG. 3A) The CD49d expression is assessed by flow cytometry every 24 hours after treatment for 72 hours. (FIG. 3B) The number of CD49d positive cells and the PE mean of fluorescence are measured. (FIG. 3C) Ratio of CD49d expression compared to control. (FIG. 3D) Ratio of the mean of fluorescence of CD49d positive cells compared to control. The FACS analysis revealed a significant decrease of surface expression of CD49d in a dose-dependent manner (57.8%±7.2 ATL1102 (10 μM) vs 99.7%±0.1 for control antisense (30 μM), P<0.001, n=3, 72 h after ATL1102 treatment). CD49d expression on mRNA level was significantly decreased by integrin α4 antisense ATL1102 treatment in HL-60 human AML cell line (85.2%±15.4 expression inhibition using ATL1102 1 μM after 24 h compared to control, p<0.001) as assessed by RT-PCR.

(FIG. 5A) The effect of ATL1102 was assessed by BrdU/7-AAD staining and revealed by flow cytometry at 48 hours after treatment. (FIG. 5B) Examples of the flow cytometric gates used for cell cycle analysis is shown for 1 μM and 30 μM ATL1102. Effect on cell cycle of HL60 cells was observed after ATL1102 treatment at above 10 μM FIG. 6. Design of mobilization assay. HL-60 cells ($5 \times 10^6$/per mouse) were injected via the tail vein in sublethally irradiated NSG mice. Presence of human cells (hCD45) was determined weekly by flow cytometry of white blood cells isolated from peripheral blood (PB). 23 Days post-leukemia injection, mice were treated with either antisense control (CTRL) (150 mg/kg, n=3), or ATL1102 (50 mg/kg, n=4). PB was drawn before and 24 hours after ATL1102-treatment. Mice to be sampled on Day 0 and treated with ATL1102 or control 24 hours later. Peripheral blood to be assayed for mobilization of mCD45/hCD45/hCD33 cells by flow cytometry. If mobilized, most of the mice are sacrificed (the first 4 groups) and organs harvested (peripheral blood, spleen and bone marrow). All the mice will be stained for an engraftment study (mCD45/hCD45/hCD33), for hCD49d and hCD29 expression and for an apoptosis (Annexin V/7AAD) and cell numbers (by Tryan blue exclusion of dead cells) will be counted with the goal to determine if the mobilized cells go back to the bone marrow, move to another organ or die in the blood (especially in the "long term" experiment). A complete blood count will also be performed using a Hemavat5/Hemanalyzer.

FIGS. 8A-C illustrate a reduced AML cancer load in mice treated with combinations of ATL1102 and Ara-C compared to Ara-C alone. FIG. 8A describes the proposed dosing schedule: four groups of six mice were dosed with Ara-C, ATL1102, control ASO or combinations of ATL1102 and Ara-C. The ATL1102 and control mice were dosed on days 3 (week 1), 11 (week 2), 18, 20 and 22 (week 3) and day 25 (week 4) and did not survive to receive the scheduled day 27 and 31 doses. The Ara-C was administered 3 times per week (days 3, 5 and 7 in week 1, days 11, 13, and 15 in week 2, days 18, 20, and 22 in week 3 and days 25, 27 and 31 in week 4) for 4 weeks. In the ATL1102 and Ara-C combination treatment, mice were dosed with Ara-C (as above) 3 times per week for 4 weeks and survived also receiving the scheduled ATL1102 doses on day 27 and 31 (week 4). Ara-C was administered at 100 mg/kg 3 times per week for the first 5 administrations and at 300 mg/kg thereafter. ATL1102 or control AS were administered at 150 mg/kg/time, once per week for the first 2 weeks followed by a scheduled 3 times per week as described above. FIG. 8B shows the bioluminescence imaging data from the ventral-abdominal side and FIG. 8C from the dorsal-back side. By day 21 there was a statistically significant (p=0.038) 61% reduction in illuminescence in the dorsal side in the combination group vs Ara-C alone and a trend 69% reduction in the ventral side (p=0.056).

FIG. 13A shows the treatment regimen: mobilization experiments were conducted with mice on day 24 of the experiments described in FIG. 8 and example 8. Mice were sacrificed 24 hours after ATL1102 or AS administration. Bone marrow, spleen and liver were harvested for hCD45 FACs analysis. FIG. 13B graphically illustrates the FACs results showing Bone marrow has 10-25% human CD45+/AML cells (i.e. vs 75-90% mouse CD45+ leukocytes), the Liver has over 90% human CD45+/AML cells, and in the spleen <5% with no differences in AS control vs ATL1102 mice at baseline or 24 hours post 150 mg/kg dose. The results show, in peripheral blood, approximately 2% vs 1% AML cells treated with AS control vs ATL1102 treated animals. This indicates U937 cells treated with ATL1102 may not be surviving in the blood (although not statistically significantly different). AML cells could be expected to move from tissues to the peripheral blood within 3 days of dosing as occurs with control. In the control, there was a statistically significant increase in the % of AML cells in the peripheral blood at day 4 vs baseline, but not in the ATL1102 treated group.

KEY TO SEQUENCE LISTING

Figure 1:
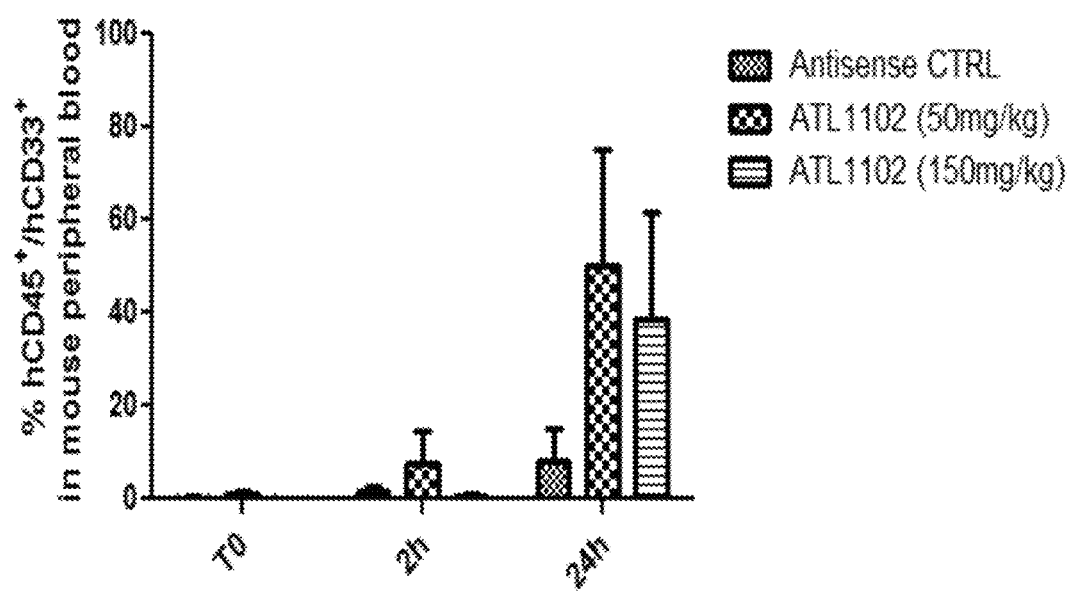
FIG. 1. ATL1102 increases AML (HL60) cells in the peripheral blood. HL-60 cells (AML; $5 \times 10^6$/per mouse) were injected via the tail vein in sublethally irradiated NSG females mice. Presence of human cells (hCD45) was determined weekly by flow cytometry of white blood cells isolated from peripheral blood. 23 Days post-leukemia injection, mice are randomly split in 3 groups treated with either antisense control (CTRL) (150 mg/kg, n=3), ATL1102 (50 mg/kg, n=4) or ATL1102 (150 mg/kg, n=3). Peripheral blood was drawn before and 2 and 24 hours after ATL-1102-treatment and white blood cells isolated and stained for murine (m) CD45, human (h) CD45 and hCD33. ATL1102 induced a strong mobilization of AML cells to the peripheral blood of leukemia-recipient mice compared to control antisense treated-mice (52.8%±45.4% vs 9.8%±15.9% at 24 h after treatment using 50 mg/kg ATL1102, n=3).

SEQ ID NO:1 Human α4 integrin antisense compound (ATL1102).
SEQ ID NO:2 Murine α4 integrin antisense compound (ISIS348574).

DESCRIPTION OF EMBODIMENTS

General Techniques and Selected Definitions

Unless specifically defined otherwise, all technical and scientific terms used herein shall be taken to have the same meaning as commonly understood by one of ordinary skill in the art (e.g., in cell culture, molecular genetics, immunology, immunohistochemistry, protein chemistry, and biochemistry).

Unless otherwise indicated, the recombinant protein, cell culture, and immunological techniques utilized in the present disclosure are standard procedures, well known to those skilled in the art. Such techniques are described and explained throughout the literature in sources such as Perbal, B. V. (1984). *A Practical Guide to Molecular Cloning*. New York: Wiley; Sambrook, J., & Green, M. R. (2012). *Molecular Cloning: A Laboratory Manual (Fourth Edition)*. New York: Cold Spring Harbour Laboratory Press; Brown, T. A. (Ed.). (1991). *Essential Molecular Biology: A Practical Approach* (Vol. 1 and 2). Oxford: IRL Press at Oxford University Press; Glover, M., & Hames, B. D. (Eds.). (1995 and 1996). *DNA Cloning: A Practical Approach* (Vols. 1-4); Ausubel, F. M. (Ed.). (1987 including all updates until present). *Current Protocols in Molecular Biology*. New York: John Wiley & Sons; Harlow, E., & Lane, D. (1988). *Antibodies: A Laboratory Manual*. New York: Cold Spring Harbor Laboratory Press; Coligan, J. E., Kruisbeek, A. M., Margulies, D. H., Shevach, E. M., & Strober, W. (Eds.). (1991 including all updates until present). *Current Protocols in Immunology*. New York: John Wiley & Sons.

The term "and/or", for example, "X and/or Y" shall be understood to mean either "X and Y" or "X or Y" and shall be taken to provide explicit support for both meanings or for either meaning.

As used herein, "about" or "approximately" shall generally mean within 20%, more preferably within 10%, and even more preferably within 5%, of a given value or range.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or group of compositions of matter.

The term "leukemia" as used herein refers to a group of cancers that usually begin in the bone marrow and result in high numbers of abnormal white blood cells. The term includes one or more of the following leukemias, acute myeloid leukemia (AML), acute lymphoblastic leukemia (ALL), acute leukemia with B cell markers (BALL), acute leukemia with T cell markers (TALL) and acute monocytic leukemia (AMoL) other acute and leukemias and chronic myeloid leukemia (CML), chronic lymphoblastic leukemia (CLL) and other chronic leukemias. This term includes all subtypes of the leukemias.

The term "acute myeloid leukemia (AML)" as used herein refers to a clonal hematopoietic disorder that may be derived from either a hematopoietic stem cell or a lineage-specific progenitor cell or a differentiated cell. AML is typically characterized both by a predominance of immature forms (with variable, but incomplete, maturation) and loss of normal hematopoiesis. Single or multiple hematopoietic lineages may comprise the leukemic clone. The requisite blast/blast equivalent percentage is typically ≥20% in the peripheral blood and bone marrow; a lower percentage is acceptable in cases with AML-defining translocations, AML with the recurrent genetic abnormalities t(15;17), t(8;21), inv(16) or t(16;16) and some cases of erythroleukemia. The blast percentage is derived from counting all nucleated cells for AML diagnosis with the exception of acute erythroid leukemias in which the blast percentage is based on non-erythroid cells. In extramedullary sites, a diagnosis of myeloid sarcoma is equivalent to AML. Blasts, blast equivalents, and other immature hematopoietic cells can be identified and distinguished from various blast look-alikes based on morphologic features, cytochemistry, or immunophenotype. For AML diagnosis, blasts include myeloblasts, monoblasts, and megakaryoblasts, while promonocytes are blast equivalents in all types of AML and promyelocytes are blast equivalents exclusively in acute promyelocytic leukemia.

The term "leukemia cell" as used herein refers to a cell that in many respects resembles a stem cell. Stem cells are clonogenic cells capable of both self-renewal and multilineage differentiation. The cells from the hematopoietic system are continually generated from self-renewing progenitors in the bone marrow called hematopoietic stem cells (HSCs). HSCs can be divided into a long-term subset, capable of indefinite self-renewal, and a short-term subset that self-renew for a defined interval. HSCs give rise to nonself-renewing oligolineage progenitors, which in turn give rise to progeny that are more restricted in their differentiation potential, and finally to functionally mature cells. Normal stem cells and leukemia cells share the ability to self-renew. Leukemia may arise from mutations that accumulate in HSCs. Alternatively, or in addition, leukemia may result from proliferation of committed progenitor cells or even differentiated cells that have reacquired stem cell characteristics, mainly the ability to self-renew. Leukemic cells commonly have one or more of increased proliferation capacity, increased self-renewal capacity, genomic instability, and impaired differentiation, resulting in increased cell survival. In one embodiment, the leukemia cells are CD34−.

The term "effective amount" as used herein refers to any dose of the antisense compound sufficient to effect leukemia cell mobilization under the conditions of administration. In one embodiment, an effective amount is additionally or alternatively any dose of the antisense compound sufficient to effect leukemia cell arrest or leukemia cell death (by, for example, apoptosis), or inhibition of leukemia cell proliferation, under the conditions of administration.

The term "mobilization" as used herein refers to movement of leukemia cells from any tissue source, for example, bone marrow, to the peripheral blood and results in an increase in the population of leukemia cells or specific subpopulations of cells in peripheral blood.

The term "cell death" refers to a process which prevents a cell from carrying out its normal metabolic functions. Cell death encompasses both apoptosis and necrosis.

The term, "apoptosis" as used herein refers to a form of cell death that includes progressive contraction of cell volume with the preservation of the integrity of cytoplasmic organelles; condensation of chromatin (i.e., nuclear condensation), as viewed by light or electron microscopy; and/or DNA cleavage into nucleosome-sized fragments, as determined by centrifuged sedimentation assays. Cell death occurs when the membrane integrity of the cell is lost (e.g., membrane blebbing) with engulfment of intact cell fragments ("apoptotic bodies") by phagocytic cells. Apoptosis may be readily determined by electron microscopy, the TUNEL assay, flow cytometry, bio imaging immunochemistry, and Western blot using DNA dyes such as propidium iodide, 7-aminoactinomycin D, BrdU Hoechst 33342 and DAPI; antibodies against cyclins, retinoblastoma and phosphorylated histone H3, cell proliferation dyes for violet and blue lasers to track cell division across multiple generations. As known to those of skill in the art, one convenient approach is to monitor the induction of annexin binding relative to control levels in an annexin binding assay. Another convenient assay employs antibodies to detect caspase 3 cleavage.

"Necrosis" (also referred to as "accidental" cell death) refers to the pathological process which occurs when cells are exposed to a serious physical or chemical insult. Necrosis occurs when cells are exposed to extreme variance from physiological conditions (e.g., hypothermia, hypoxia) which may result in damage to the plasma membrane. Necrosis begins with an impairment of the cell's ability to maintain homeostasis, leading to an influx of water and extracellular ions. Intracellular organelles, most notably themitochondria, and the entire cell swell and rupture (cell lysis).

The term "cell cycle arrest" as used herein refers to a stopping point in the cell cycle. The phases of the cell cycle start with G1, when a cell gets ready to duplicate itself. During the S phase, it actively copies its genetic material (DNA), and in G2, it has an opportunity to repair damage before M, mitosis. After mitosis, the cells can enter G1 again, or go into G0, where they rest. At each of these phases, a checkpoint temporarily halts the cell cycle to allow the cell to decide if it should continue. Sometimes, cell cycle arrest proceeds apoptosis, cell death.

The term "proliferation" as used herein refers to the process of DNA replication, growth and division, which leads to an increase in the total number of cells. Proliferation or inhibition of proliferation may readily be determined, for example by cell count, including in comparison with a population of cells that have not had proliferation inhibited, or by detection of proliferation specific cell markers, for example, the proliferation specific marker PCNA. Inhibiting proliferation or inhibition of proliferation of a cell includes rendering the cell incapable of replicating DNA, growing or dividing, or incapable of properly replicating DNA, growing or dividing, or reducing or retarding DNA replication, cell growth or division, in addition to inducing cell death by apoptosis or other mechanisms of cell death.

The term "antisense compound" as used herein refers to an oligomeric compound that hybridizes to a nucleic acid molecule encoding the α4 integrin chain of VLA-4 and/or α4β7 integrin to effect mobilization of leukemia cells. The α4 integrin chain in humans is CD49d. The antisense compound may interfere with expression of CD49d.

The term "nucleic acid molecule encoding α4 integrin" as used herein is interchangeable with "target nucleic acid" and encompasses DNA encoding the α4 integrin chain of VLA-4 or α4β7 integrin, RNA (including pre-mRNA and mRNA or portions thereof) transcribed from such DNA, and further, cDNA derived from such RNA.

The term "VLA-4" as used herein refers to a heterodimer of an α4 integrin and a β1 integrin. VLA-4 is expressed at substantial levels on peripheral blood B and T cells, thymocytes, monocytes, and other cells, as well as on hematopoietic stem and progenitor cells. Ligands for VLA-4 include vascular cell adhesion molecule-1 (VCAM-1) and CS-1, an alternately spliced domain within the Hep II region of fibronectin.

The term "α4β7 integrin" as used herein refers to a heterodimer of an α4 integrin and a β7 integrin. α4β7 integrin identifies a subset of memory T cells with a tropism for the intestinal tract. α4β7 integrin and is also expressed on a subset of mast, lymphocyte and NK progenitor cells.

α4β7 integrin is expressed on some stem and progenitor cells. Ligands for α4β7 integrin include MAdCam-1 and VCAM-1.

Antisense Compounds to α4 Integrin

The methods of the present disclosure rely on the use of an antisense compound to α4 integrin for the mobilization of leukemia cells. Such antisense compounds are targeted to nucleic acids encoding the α4 integrin chain of VLA-4 or α4β7.

Preferably, the antisense compound is an oligonucleotide. However, other oligomeric antisense compounds, including but not limited to oligonucleotide mimetics are contemplated.

Hybridization of an antisense compound with its target nucleic acid is generally referred to as "antisense". Hybridization of the antisense compound with its target nucleic acid inhibits the function of the target nucleic acid. Such "antisense inhibition" is typically based upon hydrogen bonding-based hybridization of the antisense compound to the target nucleic acid such that the target nucleic acid is cleaved, degraded, or otherwise rendered inoperable. The functions of target DNA to be interfered with can include replication and transcription. Replication and transcription, for example, can be from an endogenous cellular template, a vector, a plasmid construct or otherwise. The functions of RNA to be interfered with can include functions such as translocation of the RNA to a site of protein translation, translocation of the RNA to sites within the cell which are distant from the site of RNA synthesis, translation of protein from the RNA, splicing of the RNA to yield one or more RNA species, and catalytic activity or complex formation involving the RNA which may be engaged in or facilitated by the RNA.

"Hybridization" as used herein means pairing of complementary bases of the oligonucleotide and target nucleic acid. Base pairing typically involves hydrogen bonding, which may be Watson-Crick, Hoogsteen or reversed Hoogsteen hydrogen bonding, between complementary nucleoside or nucleotide bases (nucleobases). Guanine (G) and cytosine (C) are examples of complementary nucleobases which pair through the formation of 3 hydrogen bonds. Adenine (A) and thymine (T) are examples of complementary nucleobases which pair through the formation of 2 hydrogen bonds. Hybridization can occur under varying circumstances.

A "nucleoside" is a base-sugar combination. The base portion of the nucleoside is normally a heterocyclic base. The two most common classes of such heterocyclic bases are the purines and the pyrimidines. "Nucleotides" are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar.

"Specifically hybridizable" and "complementary" are terms which are used to indicate a sufficient degree of complementarity such that stable and specific binding occurs between the antisense compound and target nucleic acid. It is understood that the antisense compound need not be 100% complementary to its target nucleic acid sequence to be specifically hybridizable. An antisense compound is specifically hybridizable when binding of the antisense compound to the target nucleic acid interferes with the normal function of the target molecule to cause a loss of activity, and there is a sufficient degree of complementarity to avoid non-specific binding of the antisense compound to non-target sequences under conditions in which specific binding is desired, for example, under physiological conditions in the case of therapeutic treatment.

"Stringent hybridization conditions" or "stringent conditions" are terms which are used to refer to conditions under which the antisense compound will hybridize to its target sequence, but to a minimal number of other sequences. Stringent conditions are sequence-dependent and will be different in different circumstances. Stringent condition under which the antisense compound hybridizes to a target sequence is determined by the nature and composition of the antisense compound and the assays in which it is being investigated.

"Complementary" as used herein, refers to the capacity for precise pairing between a nucleobase of the antisense compound and the target nucleic acid. For example, if a nucleobase at a certain position of the antisense compound is capable of hydrogen bonding with a nucleobase at a certain position of the target nucleic acid, then the position of hydrogen bonding between the antisense compound and the target nucleic acid is considered to be a complementary position. The antisense compound may hybridize over one or more segments, such that intervening or adjacent segments are not involved in the hybridization event (e.g., a loop structure or hairpin structure). In one embodiment, the antisense compound comprises at least 70% sequence complementarity to a target region within the target nucleic acid. For example, an antisense compound in which 18 of 20 nucleobases are complementary to a target region within the target nucleic acid, and would therefore specifically hybridize, would represent 90% complementarity. In this example, the remaining noncomplementary nucleobases may be clustered or interspersed with complementary nucleobases and need not be contiguous to each other, or to complementary nucleobases. As such, an antisense compound which is 18 nucleobases in length having 4 non-complementary nucleobases which are flanked by 2 regions of complete complementarity with the target nucleic acid would have 77.8% overall complementarity with the target nucleic acid and would thus, fall within the scope of the present disclosure. Percent complementarity of an antisense compound with a region of a target nucleic acid can be determined routinely using BLAST programs (basic local alignment search tools) and PowerBLAST programs known in the art (Altschul et al., 1990; Zhang and Madden, 1997).

Antisense Oligonucleotides

The present disclosure provides antisense oligonucleotides for inhibiting expression of α4 integrin, and/or VLA-4 and/or α4β7 integrin. Such antisense oligonucleotides are targeted to nucleic acids encoding the α4 integrin chain of VLA-4 or α4b7.

The term "inhibiting expression of α4 integrin" as used herein means any measurable decrease (e.g., 10%, 20%, 50%, 90%, or 100%) in α4 integrin, VLA-4 or α4β7 integrin expression.

As used herein, the term "oligonucleotide" refers to an oligomer or polymer of RNA or DNA or mimetics, chimeras, analogs and homologs thereof. This term includes oligonucleotides composed of naturally occurring nucleobases, sugars and covalent internucleoside (backbone) linkages, as well as oligonucleotides having non-naturally occurring portions which function similarly. Such modified or substituted oligonucleotides are often preferred over native forms because of desirable properties such as, for example, enhanced cellular uptake, enhanced affinity for the target nucleic acid and increased stability in the presence of nucleases.

In forming oligonucleotides, phosphate groups covalently link adjacent nucleosides to one another to form a linear polymeric compound. In turn, the respective ends of this linear polymeric compound can be further joined to form a circular compound; however, linear compounds are generally preferred. In addition, linear compounds may have internal nucleobase complementarity and may therefore fold in a manner so as to produce a fully or partially double-stranded compound. With regard to oligonucleotides, the phosphate groups are commonly referred to as forming the internucleoside backbone of the oligonucleotide. The normal linkage or backbone of RNA and DNA is a 3' to 5' phosphodiester linkage.

Antisense oligonucleotides of the disclosure include, for example, ribozymes, siRNA, external guide sequence (EGS) oligonucleotides, alternate splicers, primers, probes, and other oligonucleotides which hybridize to at least a portion of the target nucleic acid.

Antisense oligonucleotides of the disclosure may be administered in the form of single-stranded, double-stranded, circular or hairpin and may contain structural elements such as internal or terminal bulges or loops. Once administered, the antisense oligonucleotides may elicit the action of one or more enzymes or structural proteins to effect modification of the target nucleic acid.

One non-limiting example of such an enzyme is RNAse H, a cellular endonuclease which cleaves the RNA strand of an RNA:DNA duplex. It is known in the art that single-stranded antisense compounds which are "DNA-like" elicit RNAse H. Activation of RNase H, therefore, results in cleavage of the RNA target, thereby greatly enhancing the efficiency of oligonucleotide-mediated inhibition of gene expression. Similar roles have been postulated for other ribonucleases, such as those in the RNase III and ribonuclease L family of enzymes.

The introduction of double-stranded RNA (dsRNA) molecules, has been shown to induce potent and specific antisense-mediated reduction of the function of a gene or its associated gene products. This phenomenon occurs in both plants and animals and is believed to have an evolutionary connection to viral defense and transposon silencing.

The first evidence that dsRNA could lead to gene silencing in animals came in 1995 from work in the nematode, *Caenorhabditis elegans* (Guo and Kempheus, 1995). Montgomery et al. (1998) have shown that the primary interference effects of dsRNA are posttranscriptional. The posttranscriptional antisense mechanism defined in *Caenorhabditis elegans* resulting from exposure to double-stranded RNA (dsRNA) has since been designated RNA interference (RNAi). This term has been generalized to mean antisense-mediated gene silencing involving the introduction of dsRNA leading to the sequence-specific reduction of endogenous targeted mRNA levels (Fire et al., 1998). Recently, it has been shown that it is, in fact, the single-stranded RNA oligomers of antisense polarity of the dsRNAs which are the potent inducers of RNAi (Tijsterman et al., 2002).

A person having ordinary skill in the art could, without undue experimentation, identify antisense oligonucleotides useful in the methods of the present disclosure.

Modified Internucleoside Linkages (Backbones)

Antisense compounds of the present disclosure include oligonucleotides having modified backbones or non-natural internucleoside linkages. Oligonucleotides having modified backbones include those that retain a phosphorus atom in the backbone and those that do not have a phosphorus atom in the backbone.

Modified oligonucleotide backbones containing a phosphorus atom therein include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates, and boranophosphates having normal 3'-5' linkages, 2'-5' linked analogs of these, and those having inverted polarity wherein one or more internucleotide linkages is a 3' to 3', 5' to 5' or 2' to 2' linkage.

Oligonucleotides having inverted polarity comprise a single 3' to 3' linkage at the 3'-most internucleotide linkage, that is, a single inverted nucleoside residue which may be abasic (the nucleobase is missing or has a hydroxyl group in place thereof). Various salts, mixed salts and free acid forms are also included.

Representative United States patents that teach the preparation of the above phosphorus-containing linkages include, but are not limited to, U.S. Pat. Nos. 3,687,808, 4,469,863, 4,476,301, 5,023,243, 5,177,196, 5,188,897, 5,264,423, 5,276,019, 5,278,302, 5,286,717, 5,321,131, 5,399,676, 5,405,939, 5,453,496, 5,455,233, 5,466,677, 5,476,925, 5,519,126, 5,536,821, 5,541,306, 5,550,111, 5,563,253, 5,571,799, 5,587,361, 5,194,599, 5,565,555, 5,527,899, 5,721,218, 5,672,697 and 5,625,050.

Modified oligonucleotide backbones that do not include a phosphorus atom therein include, for example, backbones formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative United States patents that teach the preparation of the above oligonucleotides include, but are not limited to, U.S. Pat. Nos. 5,034,506, 5,166,315, 5,185,444, 5,214,134, 5,216,141, 5,235,033, 5,264,562, 5,264,564, 5,405,938, 5,434,257, 5,466,677, 5,470,967, 5,489,677, 5,541,307, 5,561,225, 5,596,086, 5,602,240, 5,610,289, 5,602,240, 5,608,046, 5,610,289, 5,618,704, 5,623,070, 5,663,312, 5,633,360, 5,677,437, 5,792,608, 5,646,269 and 5,677,439.

Modified Sugar and Internucleoside Linkages

Antisense compounds of the present disclosure include oligonucleotide mimetics where both the sugar and the internucleoside linkage (i.e. the backbone), of the nucleotide units are replaced with novel groups. The nucleobase units are maintained for hybridization with the target nucleic acid.

An oligonucleotide mimetic that has been shown to have excellent hybridization properties is referred to as a peptide nucleic acid (PNA). In PNA compounds, the sugar-backbone of an oligonucleotide is replaced with an amide containing backbone, in particular, an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082, 5,714,331, and 5,719,262. Further teaching of PNA compounds can be found in Nielsen et al., 1991.

The antisense compounds of the present disclosure also include oligonucleotides with phosphorothioate backbones and oligonucleotides with heteroatom backbones, for example, —$CH_2$—NH—O—$CH_2$—, —$CH_2$—N($CH_3$)—O—$CH_2$— [known as a methylene (methylimino) or MMI backbone], —$CH_2$—O—N($CH_3$)—$CH_2$—, —$CH_2$—N($CH_3$)—N($CH_3$)—$CH_2$— and —O—N($CH_3$)—$CH_2$—$CH_2$— [wherein the native phosphodiester backbone is represented as —O—P—O—$CH_2$—] of U.S. Pat. No. 5,489,677, and the amide backbones of U.S. Pat. No. 5,602,240.

The antisense compounds of the present disclosure also include oligonucleotides having morpholino backbone structures of U.S. Pat. No. 5,034,506.

Modified Sugars

Antisense compounds of the present disclosure include oligonucleotides having one or more substituted sugar moieties.

Examples include oligonucleotides comprising one of the following at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl.

In one embodiment the oligonucleotide comprises one of the following at the 2' position: $O[(CH_2)_nO]_mCH_3$, $O(CH_2)_nOCH_3$, $O(CH_2)_nNH_2$, $O(CH_2)_nCH_3$, $O(CH_2)_nONH_2$, and $O(CH_2)_nON[(CH_2)_nCH_3]_2$, where n and m are from 1 to about 10.

Further examples include of modified oligonucleotides include oligonucleotides comprising one of the following at the 2' position: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties.

In one embodiment, the modification includes 2'-methoxyethoxy (2'-O—$CH_2CH_2OCH_3$ (also known as 2'-O-(2-methoxyethyl) or 2'-MOE) (Martin et al., 1995), that is, an alkoxyalkoxy group. In a further embodiment, the modification includes 2'-dimethylaminooxyethoxy, that is, a $O(CH_2)_2ON(CH_3)_2$ group (also known as 2'-DMAOE), or 2'-dimethylaminoethoxyethoxy (also known in the art as 2'-O-dimethyl-amino-ethoxy-ethyl or 2'-DMAEOE), that is, 2'-O—$CH_2$—O—$CH_2$—N($CH_3$)$_2$.

Other modifications include 2'-methoxy (2'-O—$CH_3$), 2'-aminopropoxy (2'-O$CH_2CH_2CH_2NH_2$), 2'-allyl (2'-$CH_2$—CH=$CH_2$), 2'-O-allyl (2'-O—$CH_2$—CH=$CH_2$) and 2'-fluoro (2'-F). The 2'-modification may be in the arabino (up) position or ribo (down) position. In one embodiment a 2'-arabino modification is 2'-F.

Similar modifications may also be made at other positions on the oligonucleotide, particularly the 3' position of the sugar on the 3' terminal nucleotide or in 2'-5' linked oligonucleotides and the 5' position of the 5' terminal nucleotide.

Oligonucleotides may also have sugar mimetics, such as cyclobutyl moieties in place of the pentofuranosyl sugar.

Representative United States patents that teach the preparation of such modified sugar structures include, but are not limited to, U.S. Pat. Nos. 4,981,957, 5,118,800, 5,319,080, 5,359,044, 5,393,878, 5,446,137, 5,466,786, 5,514,785, 5,519,134, 5,567,811, 5,576,427, 5,591,722, 5,597,909, 5,610,300, 5,627,053, 5,639,873, 5,646,265, 5,658,873, 5,670,633, 5,792,747, and 5,700,920.

A further modification of the sugar includes Locked Nucleic Acids (LNAs) in which the 2'-hydroxyl group is linked to the 3' or 4' carbon atom of the sugar ring, thereby forming a bicyclic sugar moiety. In one embodiment, the linkage is a methylene (—$CH_2$—)$_n$ group bridging the 2' oxygen atom and the 4' carbon atom, wherein n is 1 or 2. LNAs and preparation thereof are described in WO 98/39352 and WO 99/14226.

Natural and Modified Nucleobases

Antisense compounds of the present disclosure include oligonucleotides having nucleobase modifications or substitutions. As used herein, "unmodified" or "natural" nucleobases include the purine bases adenine (A) and guanine (G), and the pyrimidine bases thymine (T), cytosine (C) and uracil (U).

Modified nucleobases include other synthetic and natural nucleobases such as, for example, 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—$CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine.

Further modified nucleobases include tricyclic pyrimidines, such as phenoxazine cytidine(1H-pyrimido[5,4-b][1,4]benzoxazin-2(3H)-one), phenothiazine cytidine (1H-pyrimido[5,4-b][1,4]benzothiazin-2(3H)-one), G-clamps such as, for example, a substituted phenoxazine cytidine (e.g., 9-(2-aminoethoxy)-H-pyrimido[5,4-b][1,4]benzoxazin-2 (3H)-one), carbazole cytidine (2H-pyrimido[4,5-b]indol-2-one), pyridoindole cytidine (H-pyrido[3',2':4,5]pyrrolo[2,3-d]pyrimidin-2-one).

Modified nucleobases may also include those in which the purine or pyrimidine base is replaced with other heterocycles, for example, 7-deaza-adenine, 7-deazaguanosine, 2-aminopyridine and 2-pyridone. Further nucleobases include those disclosed in U.S. Pat. No. 3,687,808, those disclosed in J. I. Kroschwitz (editor), The Concise Encyclopedia of Polymer Science and Engineering, pages 858-859, John Wiley and Sons (1990), those disclosed by Englisch et al. (1991), and those disclosed by Y. S. Sanghvi, Chapter 15: Antisense Research and Applications, pages 289-302, S. T. Crooke, B. Lebleu (editors), CRC Press, 1993.

Certain of these nucleobases are particularly useful for increasing the binding affinity of the oligonucleotide. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. In one embodiment, these nucleobase substitutions are combined with 2'-O-methoxyethyl sugar modifications.

Representative United States patents that teach the preparation of certain of the above noted modified nucleobases as well as other modified nucleobases include, but are not limited to, U.S. Pat. Nos. 3,687,808, 4,845,205, 5,130,302, 5,134,066, 5,175,273, 5,367,066, 5,432,272, 5,457,187, 5,459,255, 5,484,908, 5,502,177, 5,525,711, 5,552,540, 5,587,469, 5,594,121, 5,596,091, 5,614,617, 5,645,985, 5,830,653, 5,763,588, 6,005,096, 5,681,941 and 5,750,692.

Conjugates

Antisense compounds of the present disclosure may be conjugated to one or more moieties or groups which enhance the activity, cellular distribution or cellular uptake of the antisense compound.

These moieties or groups may be covalently bound to functional groups such as primary or secondary hydroxyl groups.

Exemplary moieties or groups include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugate groups include cholesterols, lipids, phospholipids, biotin, phenazine, folate, phenanthridine, anthraquinone, acridine, fluoresceins, rhodamines, coumarins and dyes.

Moieties or groups that enhance the pharmacodynamic properties include those that improve uptake, enhance resistance to degradation, and/or strengthen sequence-specific hybridization with the target nucleic acid.

Moieties or groups that enhance the pharmacokinetic properties include those that improve uptake, distribution, metabolism or excretion of the compounds of the present disclosure.

Representative moieties or groups are disclosed in PCT/US92/09196 and U.S. Pat. No. 6,287,860.

Moieties or groups include but are not limited to lipid moieties such as a cholesterol moiety, cholic acid, a thioether, for example, hexyl-S-tritylthiol, a thiocholesterol, an aliphatic chain, for example, dodecandiol or undecyl residues, a phospholipid, for example, di-hexadecyl-rac-glycerol or triethylammonium 1,2-di-O-hexadecyl-rac-glycero-3-H-phosphonate, a polyamine or a polyethylene glycol chain, or adamantane acetic acid, a palmityl moiety, or an octadecylamine or hexylamino-carbonyl-oxycholesterol moiety.

Antisense compounds of the present disclosure may also be conjugated to active drug substances.

Oligonucleotide-drug conjugates and their preparation are described in U.S. Ser. No. 09/334,130.

Representative United States patents that teach the preparation of such conjugates include, but are not limited to, U.S. Pat. Nos. 4,828,979, 4,948,882, 5,218,105, 5,525,465, 5,541,313, 5,545,730, 5,552,538, 5,578,717, 5,580,731, 5,580,731, 5,591,584, 5,109,124, 5,118,802, 5,138,045, 5,414,077, 5,486,603, 5,512,439, 5,578,718, 5,608,046, 4,587,044, 4,605,735, 4,667,025, 4,762,779, 4,789,737, 4,824,941, 4,835,263, 4,876,335, 4,904,582, 4,958,013, 5,082,830, 5,112,963, 5,214,136, 5,082,830, 5,112,963, 5,214,136, 5,245,022, 5,254,469, 5,258,506, 5,262,536, 5,272,250, 5,292,873, 5,317,098, 5,371,241, 5,391,723, 5,416,203, 5,451,463, 5,510,475, 5,512,667, 5,514,785, 5,565,552, 5,567,810, 5,574,142, 5,585,481, 5,587,371, 5,595,726, 5,597,696, 5,599,923, 5,599,928 and 5,688,941.

Chimeric Compounds

As would be appreciated by those skilled in the art, it is not necessary for all positions in a given compound to be uniformly modified and in fact, more than one of the aforementioned modifications may be incorporated in a single oligonucleotide or even at a single nucleoside within an oligonucleotide.

Antisense compounds of the disclosure include chimeric oligonucleotides. "Chimeric oligonucleotides" contain two or more chemically distinct regions, each made up of at least one monomer unit, that is, a nucleotide in the case of an oligonucleotide compound. These oligonucleotides typically contain at least one region wherein the oligonucleotide is modified so as to confer upon the oligonucleotide increased resistance to nuclease degradation, increased cellular uptake, increased stability and/or increased binding affinity for the target nucleic acid. An additional region of the oligonucleotide may serve as a substrate for enzymes capable of cleaving RNA:DNA or RNA:RNA hybrids. By way of example, RNAse H is a cellular endonuclease which cleaves the RNA strand of an RNA:DNA duplex. Activation of RNase H, therefore, results in cleavage of the RNA target, thereby greatly enhancing the efficiency of oligonucleotide-mediated inhibition of gene expression. The cleavage of RNA:RNA hybrids can, in like fashion, be accomplished through the actions of endoribonucleases, such as RNAseL which cleaves both cellular and viral RNA. Cleavage of the RNA target can be routinely detected by gel electrophoresis and if necessary, associated nucleic acid hybridization techniques known in the art.

Chimeric antisense compounds of the disclosure may be formed as composite structures of two or more oligonucleotides, modified oligonucleotides, and/or oligonucleotide mimetics. Such compounds have also been referred to in the art as hybrids or gapmers.

Representative United States patents that teach the preparation of such hybrid structures include, but are not limited to, U.S. Pat. Nos. 5,013,830, 5,149,797, 5,220,007, 5,256,775, 5,366,878, 5,403,711, 5,491,133, 5,565,350, 5,623,065, 5,652,355, 5,652,356, and 5,700,922.

Exemplary Antisense Compound

In one embodiment, the antisense compound is a second generation phosphorothioate backbone 2'-MOE-modified chimeric oligonucleotide gapmer designed to hybridize to the 3'-untranslated region of VLA-4 mRNA. The oligonucleotide selectively inhibits VLA-4 expression in both primary human cells and in several human cell lines by hybridizing to RNA encoding CD49d, which is the α4 integrin subunit of VLA-4 and α4β7 integrin.

The oligonucleotide is the 19-sodium salt of a 3'→5' phosphorothioate oligonucleotide 20mer also referred as a 3-9-8 MOE gapmer having a molecular weight of 7230 Daltons, in which the nucleotides at positions 1 to 3 from the 5' end are 2'-O-(2-methoxyethyl) (2'MOE) modified ribonucleosides (2'-O-(2-methoxyethyl ribose); the nucleotides at positions 4 to 12 from the 5' end are 2'-deoxyribonucleosides of which all cytosines are 5-methylcytosines; the nucleotides at positions 13 to 20 from the 5' end are 2'-O-(2-methoxyethyl) modified ribonucleosides.

The sequence of the oligonucleotide is:

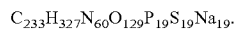
(SEQ ID NO: 1).

The empirical formula of the oligonucleotide is:

$C_{233}H_{327}N_{60}O_{129}P_{19}S_{19}Na_{19}$.

All uracils are 5-methyluracils ($^{Me}U$). Typically, the oligonucleotide is synthesized using 2-methoxyethyl modified thymidines not 5-methyluracils.

All pyrimidines are C5 methylated (i.e U, T, C are C5 methylated).

Nomenclature

The sequence of the oligonucleotide may be named by accepted oligonucleotide nomenclature, showing each O-O linked phosphorothioate internucleotide linkage:
2'-O-methoxyethyl-5-methylcytidylyl-(3'→5' O, O-phosphorothioyl)-2'-O-methoxyethyl-5-methyluridylyl-(3'→5' O, O-phosphorothioyl)-2'-O-methoxyethylguanosylyl-(3'→5' O, O-phosphorothioyl)-2'-O-deoxyadenosylyl-(3'→5' O, O-phosphorothioyl)-2'-O-deoxyguanosylyl-(3'→5' O, O-phosphorothioyl)-thymidylyl-(3'→5' O, O-phosphorothioyl)-2'-deoxy-5-methylcytidylyl-(3'→5' O, O-phosphorothioyl)-thymidylyl-(3'→5' O, O-phosphorothioyl)-2'-deoxyguanosylyl-(3'→5' O, O-phosphorothioyl)-thymidylyl-(3'→5' O, O-phosphorothioyl)-thymidylyl-(3'→5' O, O-phosphorothioyl)-thymidylyl-(3'→5' O, O-phosphorothioyl)-2'-O-methoxyethyl-5-methyluridylyl-(3'→5' O, O-phosphorothioyl)-2'-methoxyethyl-5-methylcytidylyl-(3'→5' O, O-phosphorothioyl)-2'-methoxyethyl-5-methylcytidylyl-(3'→5' O, O-phosphorothioyl)-2'-O-methoxyethyl-5-adenosylyl-(3'→5' O, O-phosphorothioyl)-2'-O-methoxyethyl-5-methyluridylyl-(3'→5' O, O-phosphorothioyl)-2'-O-methoxyethyl-5-methyluridylyl-(3'→5' O, O-phosphorothioyl)-2'-O-methoxyethyl-5-methylcytosine, (3'→5' O, O-phosphorothioyl)-2'-O-methoxyethyl-5-methyluridylyl-19 sodium salt.

Synthesis

The oligonucleotide may be synthesized by a multi-step process that may be divided into two distinct operations: solid-phase synthesis and downstream processing. In the first operation, the nucleotide sequence of the oligonucleotide is assembled through a computer-controlled solid-phase synthesizer. Subsequent downstream processing includes deprotection steps, preparative reversed-phase chromatographic purification, isolation and drying to yield the oligonucleotide drug substance. The chemical synthesis of the oligonucelotide utilizes phosphoramidite coupling chemistry followed by oxidative sulfurization and involves sequential coupling of activated monomers to an elongating oligomer, the 3'-terminus of which is covalently attached to the solid support.

Detritylation (Reaction a).

Each cycle of the solid-phase synthesis commences with removal of the acid-labile 5'-O-4, 4'-dimethoxytrityl (DMT) protecting group of the 5' terminal nucleoside of the support bound oligonucleotide. This is accomplished by treatment with an acid solution (for example dichloroacetic acid (DCA) in toluene). Following detritylation, excess reagent is removed from the support by washing with acetonitrile in preparation for the next reaction.

Coupling (Reaction b)

Chain elongation is achieved by reaction of the 5'-hydroxyl group of the support-bound oligonucleotide with a solution of the phosphoramidite corresponding to that particular base position (e.g., for base2: MOE-$^{Me}$C amidite) in the presence of an activator (e.g., 1H-tetrazole). This results in the formation of a phosphite triester linkage between the incoming nucleotide synthon and the support-bound oligonucleotide chain. After the coupling reaction, excess reagent is removed from the support by washing with acetonitrile in preparation for the next reaction.

Sulfurization (Reaction c)

The newly formed phosphite triester linkage is converted to the corresponding [O, O, O)-trialkyl phosphorothioate triester by treatment with a solution of a sulfur transfer reagent (e.g., phenylacetyl disulfide). Following sulfurization, excess reagent is removed from the support by washing with acetonitrile in preparation for the next reaction.

Capping (Reaction d)

A small proportion of the 5'-hydroxy groups available in any given cycle fail to extend. Coupling of these groups in any of the subsequent cycles would result in formation of process-related impurities ("DMT-on (n-1)-mers") which are difficult to separate from the desired product. To prevent formation of these impurities and to facilitate purification, a "capping reagent" (e.g., acetic anhydride and N-methylimidazole/acetonitrile/pyridine) is introduced into the reactor vessel to give capped sequences. The resulting failure sequences ("DMT-off shortmers") are separated from the desired product by reversed phase HPLC purification. After the capping reaction, excess reagent is removed from the support by washing with acetonitrile in preparation of the next reaction.

Reiteration of this basic four-step cycle using the appropriate protected nucleoside phosphoramidite allows assembly of the entire protected oligonucleotide sequence.

Backbone Deprotection (Reaction e)

Following completion of the assembly portion of the process the cyanoethyl groups protecting the (O, O, O)-trialkyl phosphorothioate triester internucleotide linkages are removed by treatment with a solution of triethylamine (TEA) in acetonitrile. The reagent and acrylonitrile generated during this step are removed by washing the column with acetonitrile.

Cleavage from Support and Base Deprotection (Reaction f)

Deprotection of the exocyclic amino groups and cleavage of the crude product from the support is achieved by incubation with aqueous ammonium hydroxide (reaction f). Purification of the crude, 5'-O-DMT-protected product is accomplished by reversed phase HPLC. The reversed phase HPLC step removes DMT-off failure sequences. The elution profile is monitored by UV absorption spectroscopy. Fractions containing DMT-on oligonucleotide product are collected and analyzed.

Acidic Deprotection (Reaction g)

Reversed phase HPLC fractions containing 5'-O-DMT-protected oligonucleotide are pooled and transferred to a precipitation tank. The products obtained from the purification of several syntheses are combined at this stage of the process. Purified DMT-on oligonucleotide is treated with acid (e.g., acetic acid) to remove the DMT group attached to the 5' terminus. After acid exposure for the prescribed time and neutralization, the oligonucleotide drug substance is isolated and dried.

Following the final acidic deprotection step, the solution is neutralized by addition of aqueous sodium hydroxide and the oligonucleotide drug substance is precipitated from solution by adding ethanol. The precipitated material is allowed to settle at the bottom of the reaction vessel and the ethanolic supernatant decanted. The precipitated material is redissolved in purified water and the solution pH adjusted to between pH 7.2 and 7.3. The precipitation step is repeated. The precipitated material is dissolved in water and the solution filtered through a 0.45 micron filter and transferred into disposable polypropylene trays that are then loaded into a lyophilizer. The solution is cooled to −50° C. Primary drying is carried out at 25° C. for 37 hours. The temperature is increased to 300° C. and a secondary drying step performed for 5.5 hours. Following completion of the lyophilization process, the drug substance is transferred to high density polyethylene bottles and stored at −200° C.

Target Nucleic Acid

"Targeting" an antisense compound to a particular nucleic acid can be a multistep process. The process usually begins with the identification of a target nucleic acid whose function is to be modulated. In the present disclosure, the target nucleic acid encodes the α4 integrin chain of VLA-4 or α4β7 integrin.

The targeting process usually also includes determination of at least one target region, segment, or site within the target nucleic acid for the antisense interaction to occur such that the desired effect, for example, inhibition of expression, will result. The term "region" as used herein is defined as a portion of the target nucleic acid having at least one identifiable structure, function, or characteristic. Within regions of the target nucleic acids are segments. "Segments" are defined as smaller or sub-portions of regions within a target nucleic acid. "Sites" as used herein, means positions within the target nucleic acid.

Since the "translation initiation codon" is typically 5'-AUG (in transcribed mRNA molecules; 5'-ATG in the corresponding DNA molecule), the translation initiation codon is also referred to as the "AUG codon", the "start codon" or the "AUG start codon". A minority of genes have a translation initiation codon having the RNA sequence 5'-GUG, 5'-UUG, or 5'-CUG, and 5'-AUA, 5'-ACG and 5'-CUG have been shown to function in vivo. Thus, the terms "translation initiation codon" and "start codon" can encompass many codon sequences even though the initiator amino acid in each instance is typically methionine (in eukaryotes) or formylmethionine (in prokaryotes). It is also known in the art that eukaryotic and prokaryotic genes may have two or more alternative start codons, any one of which may be preferentially utilized for translation initiation in a particular cell type or tissue, or under a particular set of conditions. The terms "start codon" and "translation initiation codon" as used herein refer to the codon or codons that are used in vivo to initiate translation of an mRNA transcribed from a gene encoding, for example, α4 integrin chain of VLA-4 or α4β7 integrin, regardless of the sequence(s) of such codons.

A "translation termination codon" also referred to a "stop codon" may have one of three RNA sequences: 5'-UAA, 5'-UAG and 5'-UGA (5'-TAA, 5'-TAG and 5'-TGA, respectively in the corresponding DNA molecule). The terms "translation termination codon" and "stop codon" as used herein refer to the codon or codons that are used in vivo to terminate translation of an mRNA transcribed from a gene encoding the α4 integrin chain of VLA-4 or α4β7 integrin, regardless of the sequence(s) of such codons.

The terms "start codon region" and "translation initiation codon region" refer to a portion of the mRNA or gene that encompasses from about 25 to about 50 contiguous nucleotides in either direction (i.e., 5' or 3') from the translation initiation codon. Similarly, the terms and "stop codon region" and "translation termination codon region" refer to a portion of the mRNA or gene that encompasses from about 25 to about 50 contiguous nucleotides in either direction (i.e., 5' or 3') from the translation termination codon. Consequently, the "start codon region" or "translation initiation codon region" and the "stop codon region" or "translation termination codon region" are all regions which may be targeted effectively with the antisense compounds of the present disclosure.

The "open reading frame" (ORF) or "coding region", which is known in the art to refer to the region between the translation initiation codon and the translation termination codon, is also a region which may be targeted effectively. In one embodiment, the intragenic region encompassing the translation initiation or termination codon of the ORF of a gene is targeted.

Other target regions include the 5' untranslated region (5'UTR), known in the art to refer to the portion of the mRNA in the 5' direction from the translation initiation codon, and thus including nucleotides between the 5' cap site and the translation initiation codon of the mRNA (or corresponding nucleotides on the gene), and the 3' untranslated region (3'UTR), known in the art to refer to the portion of the mRNA in the 3' direction from the translation termination codon, and thus including nucleotides between the translation termination codon and 3' end of the mRNA (or corresponding nucleotides on the gene). The 5' cap site of an mRNA comprises an N7-methylated guanosine residue joined to the 5'-most residue of the mRNA via a 5'-5' triphosphate linkage. The 5' cap region of an mRNA is considered to include the 5' cap structure itself, as well as the first 50 nucleotides adjacent to the cap site. In one embodiment, the 5' cap region is targeted.

Although some eukaryotic mRNA transcripts are directly translated, many contain one or more regions, known as "introns," which are excised from a transcript before it is translated. The remaining (and therefore translated) regions are known as "exons" and are spliced together to form a continuous mRNA sequence. mRNA transcripts produced via the process of splicing of two (or more) mRNAs from different gene sources are known as "fusion transcripts". In one embodiment, introns, or splice sites, that is, intron-exon junctions or exon-intron junctions, or aberrant fusion junctions due to rearrangements or deletions are targeted.

Alternative RNA transcripts can be produced from the same genomic region of DNA. These alternative transcripts are generally known as "variants".

"Pre-mRNA variants" are transcripts produced from the same genomic DNA that differ from other transcripts produced from the same genomic DNA in either their start or stop position and contain both intronic and exonic sequence. Upon excision of one or more exon or intron regions, or portions thereof during splicing, pre-mRNA variants produce smaller "mRNA variants". Consequently, mRNA variants are processed pre-mRNA variants and each unique pre-mRNA variant must always produce a unique mRNA variant as a result of splicing. These mRNA variants are also known as "alternative splice variants". If no splicing of the pre-mRNA variant occurs then the pre-mRNA variant is identical to the mRNA variant.

Variants can be produced through the use of alternative signals to start or stop transcription, that is through use of an alternative start codon or stop codon. Variants that originate from a pre-mRNA or mRNA that use alternative start codons are known as "alternative start variants" of that pre-mRNA or mRNA. Those transcripts that use an alternative stop codon are known as "alternative stop variants" of that pre-mRNA or mRNA. One specific type of alternative stop variant is the "polyA variant" in which the multiple transcripts produced result from the alternative selection of one of the "polyA stop signals" by the transcription machinery, thereby producing transcripts that terminate at unique polyA sites. In one embodiment, the pre-mRNA or mRNA variants are targeted.

The location on the target nucleic acid to which the antisense compound hybridizes is referred to as the "target segment". As used herein the term "target segment" is defined as at least an 8-nucleobase portion of a target region to which an antisense compound is targeted. While not wishing to be bound by theory, it is presently believed that these target segments represent portions of the target nucleic acid which are accessible for hybridization.

Once one or more target regions, segments or sites have been identified, antisense compounds are chosen which are sufficiently complementary to a target segment, that is, antisense compounds that hybridize sufficiently well and with sufficient specificity, to give the desired effect.

In a further embodiment, the target segment identified herein may be employed in a screen for additional compounds that modulate the expression of the α4 integrin gene (and thus expression of α4 integrin, VLA-4 and/or α4β7 integrin). "Modulators" are those compounds that decrease or increase the expression of a nucleic acid molecule encoding the α4 integrin chain of VLA-4 or α4β7 integrin and which comprise at least a 8 nucleobase portion which is complementary to a preferred target segment.

The screening method comprises the steps of contacting a target segment of the nucleic acid encoding the α4 integrin chain of VLA-4 or α4β7 integrin with one or more candidate modulators, and selecting for one or more candidate modulators which decrease or increase the expression of a nucleic acid encoding the α4 integrin chain of VLA-4 or α4β7 integrin. Once it is shown that the candidate modulator or modulators are capable of modulating (e.g., either decreasing or increasing) the expression of a nucleic acid encoding the α4 integrin chain of VLA-4 or α4β7 integrin, the modulator may then be employed in further investigative studies of the function of VLA-4 or α4β7 integrin, or for use as a research, diagnostic, or therapeutic agent.

The target segment may also be combined with its respective complementary antisense compound to form stabilized double-stranded (duplexed) oligonucleotides.

Such double stranded oligonucleotide moieties have been shown in the art to modulate target expression and regulate translation, as well as RNA processing via an antisense mechanism. Moreover, the double-stranded moieties may be subject to chemical modifications (Fire et al., 1998; Timmons and Fire, 1998; Timmons et al., 2001; Tabara et al., 1998; Montgomery et al., 1998; Tuschl et al., 1999; Elbashir et al., 2001a; Elbashir et al., 2001b). For example, such double-stranded moieties have been shown to inhibit the target by the classical hybridization of antisense strand of the duplex to the target, thereby triggering enzymatic degradation of the target (Tijsterman et al., 2002).

Compositions

Antisense compounds of the disclosure may be admixed, encapsulated, conjugated or otherwise associated with other molecules, molecule structures or mixtures of compounds, resulting in, for example, liposomes, receptor-targeted molecules, oral, rectal, topical or other formulations, for assisting in uptake, distribution and/or absorption.

Representative United States patents that teach the preparation of such uptake, distribution and/or absorption-assisting formulations include, but are not limited to, U.S. Pat. Nos. 5,108,921, 5,354,844, 5,416,016, 5,459,127, 5,521, 291, 5,543,158, 5,547,932, 5,583,020, 5,591,721, 4,426,330, 4,534,899, 5,013,556, 5,108,921, 5,213,804, 5,227,170, 5,264,221, 5,356,633, 5,395,619, 5,416,016, 5,417,978, 5,462,854, 5,469,854, 5,512,295, 5,527,528, 5,534,259, 5,543,152, 5,556,948, 5,580,575, and 5,595,756.

Antisense compounds of the disclosure may be administered in a pharmaceutically acceptable carrier. The term "pharmaceutically acceptable carrier" refers to molecular entities that do not produce an allergic, toxic or otherwise adverse reaction when administered to a subject, particularly a mammal, and more particularly a human. The pharmaceutically acceptable carrier may be solid or liquid. Useful examples of pharmaceutically acceptable carriers include, but are not limited to, diluents, solvents, surfactants, excipients, suspending agents, buffering agents, lubricating agents, adjuvants, vehicles, emulsifiers, absorbants, dispersion media, coatings, stabilizers, protective colloids, adhesives, thickeners, thixotropic agents, penetration agents, sequestering agents, isotonic and absorption delaying agents that do not affect the activity of the active agents of the disclosure.

Antisense compounds of the disclosure may be pharmaceutically acceptable salts, esters, or salts of the esters, or any other compounds which, upon administration are capable of providing (directly or indirectly) the biologically active metabolite.

The term "pharmaceutically acceptable salts" as used herein refers to physiologically and pharmaceutically acceptable salts of the antisense compounds that retain the desired biological activities of the parent compounds and do not impart undesired toxicological effects upon administration. Preferred examples of pharmaceutically acceptable salts and their uses are further described in U.S. Pat. No. 6,287,860.

Antisense compounds of the disclosure may be prodrugs or pharmaceutically acceptable salts of the prodrugs, or other bioequivalents.

The term "prodrugs" as used herein refers to therapeutic agents that are prepared in an inactive form that is converted to an active form (i.e., drug) upon administration by the action of endogenous enzymes or other chemicals and/or conditions. In particular, prodrug forms of the antisense compounds of the disclosure are prepared as SATE [(S-acetyl-2-thioethyl) phosphate] derivatives according to the methods disclosed in WO 93/24510, WO 94/26764 and U.S. Pat. No. 5,770,713.

Administration

The present inventors have found that leukemia cells can be mobilized to the peripheral blood using an antisense compound that inhibits α4 integrin expression and/or VLA-4 and/or α4β7 integrin expression. Detachment of leukemia cells from the bone marrow alone or in combination with drug therapy (e.g., chemotherapy) can be used to improve outcome of therapy for leukemia.

Detachment of AML cells from the bone marrow alone or in combination with drug therapy (e.g., chemotherapy) can be used to improve outcome of therapy for AML.

The antisense compounds of the disclosure are administered systemically. As used herein "systemic administration" is a route of administration that is either enteral or parenteral.

As used herein "enteral" refers to any form of administration that involves any part of the gastrointestinal tract and includes oral administration of, for example, the antisense oligonucleotide in tablet, capsule or drop form; gastric feeding tube, duodenal feeding tube, or gastrostomy; and rectal administration of, for example, the antisense compound in suppository or enema form.

As used herein "parenteral" includes administration by injection or infusion. Examples include, intravenous (into a vein), intravenous bolus, intraarterial (into an artery), intramuscular (into a muscle), subcutaneous (under the skin), intraosseous infusion (into the bone marrow), intradermal, (into the skin itself), intraperitoneal (infusion or injection into the peritoneum), transdermal (diffusion through the intact skin), transmucosal (diffusion through a mucous membrane), inhalational. Subcutaneous, intraperitoneal and intravenous bolus routes are preferred. The intravenous bolus route is particularly preferred.

The antisense compound may be administered as single dose or as repeated doses on a period basis, for example, daily, weekly, or monthly.

The amount and frequency of administration may be determined by an attending physician or veterinarian. By way of example, a dose of 50-1600 mg antisense compound may be administered to a subject. A dose of 150-450 mg is particularly contemplated for humans. A dose of 2-6 mg/Kg is also particularly contemplated. In one embodiment, the antisense compound is administered once daily or twice daily for a week.

In one embodiment, the antisense compound is dosed at 50 mg, or 100 mg, or 200 mg, or 300 mg, or 400 mg, or 500 mg at a frequency of once weekly, or once fortnightly, or once every three weeks, or once every 28 days.

In another embodiment, the antisense compound is dosed at 50 mg, or 100 mg, or 200 mg, or 300 mg, on two or more days per week to effect mobilization of leukemia cells.

In another embodiment, the antisense compound is dosed at 300 mg every other day to effect leukemia cell arrest, or leukemia cell death (by, for example, apoptosis), or inhibition of leukemia cell proliferation.

Combination Therapy

Antisense compounds of the disclosure may be administered in combination with one or more therapeutic agents to treat leukemia, for example, AML.

In one embodiment, CD49d expression levels are used as a potential predictive response biomarker for the subject treatment.

As used herein, the term "treat" or "treatment" includes abrogating, inhibiting, slowing, or reversing the progression of a disease or condition, or ameliorating or preventing a clinical symptom of the disease or condition.

Exemplary therapeutic agents include cytotoxic agents, chemotherapeutic agents, drugs such as an anthracycline, immunooncolytic agents, such as those that induce an ADCC, and immunoconjugates. Illustrative immunoconjugates include an antibody or an antigen binding part thereof targeted to leukemia cells and conjugated to one or more cytotoxic, chemotherapeutic, growth inhibitory agent or radioactive isotope. In one embodiment, an immunoconjugate is an antibody-drug conjugate (ADC) wherein the antibody or antigen binding portion thereof is conjugated to a drug, such as a maytansinoid, an auristatin, a dolastatin, a calicheamicin, an anthracycline, anthracenedione, cytarabine, methotrexate, vindesine, a taxane, a trichothecene etc.

Chemotherapeutic therapy may comprise remission induction followed by post remission chemotherapy. Induction therapy is given with the goal of decreasing the number of leukemia cells to an undetectable level and restoring the production of normal blood cells.

In one embodiment, the chemotherapeutic agent is cytarabine. Cytarabine may be given continuously for seven days through an intravenous (IV) line. Typically an anthracycline drug, such as daunorubicin, idarubicin or mitoxantrone, can also be given in a single IV dose for the first three days of treatment. This is sometimes known as the "7+3" regimen. Typically, the 7+3 regimen comprises administering 100 mg/m$^2$ cytarabine for 7 days plus an anthracycline or anthracenedione (most often daunorubicin, 45 mg/m$^2$ in older adults, 90 mg/m$^2$ in younger adults, but other options include 12 mg/m$^2$ idarubicin or mitoxantrone) for 3 days.

Commonly, a bone marrow biopsy will be repeated 2 weeks following the initiation of therapy, to assess marrow aplasia. If residual leukemia is detected, patients are treated with another chemotherapy course, termed reinduction.

Postremission chemotherapy then aims to eradicate any residual disease in an attempt at cure. Postremission chemotherapy may comprise high-dose cytarabine (Ara-C; HiDAC). Typically, the HiDAC regimen comprises administering 1,000 to 3,000 mg/m$^2$ cytarabine IV over 1 to 3 hours every 12 hours for 6 to 12 doses.

In one embodiment, chemotherapy will comprise high dose cytarabine (Ara-C) treatment. In one embodiment, 3 g/m$^2$/day Ara-C is administered intravenously over 3 hours, on Days 2-6 to patients ≤60 years and 1.5 g/m$^2$/day Ara-C is administered intravenously over 3 hours, on Days 2-6 to patients >60 years. Bone marrow biopsy and aspiration is performed on Day 30 (±2 days). In patients who do not show sufficient bone marrow recovery by Day 30 (in the absence of leukemia cells), bone marrow biopsy and aspiration will be repeated 1-2 weeks later. Additional bone marrow aspirations may be performed at the attending physician's discretion to assess response. Patients who have persistent disease after the first cycle can receive reinduction at the full doses of antisense compound/Ara-C. Patients achieving complete remission (CR), complete remission except for recovery of platelet counts (CRp) or partial response (PR) after first cycle of therapy will receive additional cycle of antisense compound/Ara-C with full dose of antisense compound and a 25% reduction of Ara-C doses. The response assessment will be after two cycles of therapy. Patients achieving CR, CRp or PR after two cycles of therapy can continue with consolidation or maintenance as per attending physician's discretion, without antisense compound. The full dose in man is typically established during Phase 1 dose escalation trials to determine the minimum therapeutic dose. Administration may be provided a doses of about 150-450 mg in man. A dose of 2-6 mg/Kg is also particularly contemplated for human subjects. In one embodiment, the antisense compound is administered once daily or twice daily for a week. In one embodiment, the antisense compound is dosed at 50 mg, or 100 mg, or 200 mg, or 300 mg, or 400 mg, or 500 mg at a frequency of once weekly, or once fortnightly, or once every three weeks, or once every 28 days. In one embodiment, the antisense compound is dosed at 50 mg, or 100 mg, or 200 mg, or 300 mg on two or more days a week to effect mobilization of leucocyte cells. In one embodiment, the antisense compound is dosed at 300 mg on two or more days a week to effect leukemia cell arrest, or leukemia cell death (by, for example, apoptosis), or inhibition of leukemia cell proliferation.

Other chemotherapy treatments include high dose Ara-C/Mitoxantrone, 2-Idarubicine/Flag (or Flag alone if no more anthracycline can be given) (Flag: fludarabine+high-dose cytarabine+G-CSF), and 3-CLO/VP16 (etoposide)/CTX (or Clo/Ara-C).

The therapeutic agent may be administered prior to, subsequently, or concurrently with the antisense compound. In one embodiment, the therapeutic agent will be administered subsequent to administration of the antisense compound, when maximal mobilization of leukemia cells to the peripheral blood is expected, for example, 24-36 hours after the first dose of the antisense compound. In a preferred embodiment, the up to 450 mg or 6 mg/kg antisense compound is administered iv on Day 1, 3 g/m$^2$/day Ara-C administered intravenously over 3 hours, on Days 2-6 to patients ≤60 years and 1.5 g/m$^2$/day Ara-C is administered intravenously over 3 hours, on Days 2-6 to patients >60 years.

In one embodiment, the therapeutic agent is first administered when there is >20% leukemia blasts in the peripheral blood (i.e., a High leukemia burden). CR, CRp, and PR are terms understood by those skilled in the art.

Hematologic, morphologic, cytochemical or immunophenotypic analysis can be used to determine the level of leukemia cells in the peripheral blood prior to, subsequent to, or during treatment with a therapeutic agent.

Blood or bone marrow smears may be morphologically examined using a May-Grunwald-Gimsa or a Wright-Gimsa stain. Typically, at least 200 leukocytes on blood smears and 500 nucleated cells on marrow smears are counted, with the latter containing spicules. Myeloblasts, monoblasts, and megakaryoblasts are included in the blast count. In AML with monocytic or myelomonocytic differentiation, monoblasts and promonocytes, but not abnormal monocytes, are counted as blast equivalents. Erythroblasts are not counted as blasts except in the rare instance of pure erythroid leukemia.

Cytochemistry using myeloperoxidase (MPO) or Sudan black B (SBB) and nonspecific esterase (NSE) stains can be used to identify lineage involvement. Detection of MPO (if present in $\geq 3\%$ of blasts) typically indicates myeloid differentiation, but its absence does not exclude a myeloid lineage because early myeloblasts and monoblasts may lack MPO. SBB staining parallels MPO but is less specific. NSE stains show diffuse cytoplasmic activity in monoblasts (usually >80% positive) and monocytes (usually >20% positive). In acute erythroid leukemia, a periodic acid-Schiff (PAS) stain may show large globules of PAS positivity. Iron stains may allow for the detection of iron stores, normal sideroblasts, and ring sideroblasts.

Alternatively, or in addition to cytochemistry, immunophenotyping may be used to determine lineage involvement. Quantification of expression patterns of several surface and cytoplasmic antigens is typically required for lineage assignment.

Precursor stage markers include, for example, CD34, CD38, CD117, CD133, and HLA-DR. Granulocytic markers include, for example, CD13, CD15, CD16, CD33, CD65, and cytoplasmic myeloperoxidase (cMPO). Monocytic markers include, for example, nonspecific esterase (NSE), CD11c, CD14, CD64, lysozyme, CD4, CD11b, CD36, and NG2 homologue. Megakaryocytic markers include, for example, CD41 (glycoprotein IIb/IIIa), CD61 (glycoprotein IIIa), and CD42 (glycoprotein 1b). Erythroid markers include, for example, CD235a (glycophorin A). Myeloid lineage markers include, for example, MPO or evidence of monocytic differentiation (at least two of NSE, CD11c, CD14, CD64 and lysozyme). B-lineage markers include CD19 (strong) with at least one of the following: CD79a, CD22, CD10, or CD19 (weak) with at least two of the following CD79a, cCD22, C10. T-lineage markers include, for example, cCD3 or surface CD3. In one embodiment, the number of CD123+, CD34+ and CD38− cells is assayed by, for example, flow cytometry.

An acute leukemia is typically considered positive for a marker if $\geq 20\%$ leukemia cells express the marker. For some markers (e.g., (e.g., cytoplasmic CD3, MPO, TdT, CD34, CD117) a lower cutoff of 10% may be applied.

Chromosome abnormalities are detected in leukemias. A minimum of 20 metaphase cells analyzed from bone marrow is typically considered necessary to establish the diagnosis of a normal karyotype, and recommended to define an abnormal karyotype. Abnormal karyotypes may be diagnosed from blood specimens.

Fluorescence in situ hybridization (FISH) is an option to detect gene rearrangements, such as RUNX1-RUNX1T1, CBFB-MYH11, MLL and EVI1 gene fusions, or loss of chromosome 5q and 7q material. FISH is frequently necessary to identify MLL fusion partners in 11q23 translocations.

Molecular diagnosis by reverse transcriptase-polymerase chain reaction (RT-PCR) for the recurring gene fusions, such as RUNX1-RUNXIT1, CBFB-MYH11, MLLT3-MLL, DEK-NUP214, can be useful in certain circumstances.

Example 1

Methods

ATL1102. ATL1102 is 20 bases in length, with a molecular weight of 7230 Da. It is the 19-sodium salt of a 3'→5' phosphorothioate oligonucleotide 20-mer with a 3-9-8, 2'-O-(2-methoxyethyl) gapmer design to support an RNase H antisense mechanism of action. The ATL1102 sequence is 5'-$^{Me}C^{Me}C$UG AGT $^{Me}C$TG TTT $^{Me}U^{Me}C^{Me}C$ A$^{Me}U^{Me}$U $^{Me}C^{Me}$U-3'(SEQ ID NO: 1), with the first 3 and last 8 bases 2'-O-(2-methoxyethyl) modified and cytosine and uracil bases 5'methylated (Me).

ATL1102 in vitro. AML cells (HL60) were nucleoporated using Amaxa Cell line Nucleofector Kit V (Lonza) and treated with various concentrations of ATL1102 or scrambled control.

Mobilization of AML cells using ATL1102 in vivo. To determine the mobilization effect, HL60 cells were injected into NSG mice (1.3-5×10$^6$ cells/mouse; n=/group). Mice were treated with a single dose of ATL1102 or scramble control on Day 23 post-leukemia injection. White blood cells from femurs, spleen, and peripheral blood were analyzed at various time points post-antisense treatment and stained with human CD19 and CD45 antibodies to distinguish human pre-B ALL cells from mouse recipient cells.

Leukemia samples. HL60 was obtained from Dr. Nora Heisterkamp., CHLA. Bone marrow and peripheral blood samples from AML patients were provided by USC (Los Angeles, USA), in compliance with the Institutional Review Board regulations of each institution. Informed consent was obtained from all human subjects.

Xenograft model of primary leukemia. Under IACUC approved protocols, NOD.Cg-Prkdc$^{scid}$ IL2rg$^{tm1Wjl}$/SzJ (NSG) mice of 5-7 weeks of age were conditioned with a single sub-lethal dose of 250 cGy of whole body irradiation (250 cGy), followed by intravenous injection of 1.3-5× 10$^6$HL60 cells per mouse. Matsunaga et al. Nature Medicine 2003; 9:1158-1165. Mice were monitored for weight change and presence of bioluminescent signaling by bioimaging and human CD45$^+$ cells expression in the peripheral blood by flow cytometry. White blood cells (WBC) from peripheral blood, spleen, and bone marrow were then isolated.

In vivo imaging. Primary ALL cells were labelled with luciferase by transduction with pCCL-MNDU3-LUC viral supernatant. Monitoring of leukemia progression by determining bioluminescence signal development in mice was performed as previously described. Park et al. Blood (2011) 118:2191-2199.

In Vivo treatment with chemotherapy. In a xenograft model of AML, NSG mice are treated with 1.5 mg/kg doxorubicin for 3 days, 50 mg/kg Ara-C for 5 days by intravenous co-delivery of both drugs (Wunderlich et al. Blood (2013) 121:e90-e97).

White blood cell isolation from mouse organs. For mobilization assays, femurs, spleens were harvested in cold PBS peripheral blood, and peripheral blood by tail vein bleeding. The white blood cell isolation from femurs, spleen, and peripheral blood were obtained by Red Blood Cell Lysis using Ammonium chloride. The resulting single cell suspension was kept in cold IMDM media, plus 20% FBS for further analysis.

CBC counts. Peripheral blood was withdrawn via the tail vein for CBC analysis from mice when they were sacrificed. Blood samples (~100 μl/sample) were collected in BD microtainer tubes with EDTA (BD Biosciences) and analyzed on a hemanalyzer, Hemavet VetScan HM5 cell counter (Abaxis, Union City, Calif.).

Flow cytometry. Anti-human CD45-FITC (HI130) and anti-mouse CD45-PE (30-F11) antibodies as well as respective isotype controls (clones MOPC-21 and A95-1) and Annexin V, PI and 7-AAD for apoptosis and BrdU for cell cycle analyses were obtained from BD Biosciences (San Jose, Calif.).

Quantitative real-time PCR. RNA samples were isolated using RNeasy Plus MiniKits (Qiagen, Hilden, Germany), with subsequent cDNA synthesis. Quantitative real-time PCR was performed by mixing cDNA samples with the SYBR GreenER (Invitrogen). The samples were loaded into an optical 96-well reaction plate (Applied Biosystems, Foster City, Calif.) and analyzed by ABI7900HT real-time PCR system (Applied Biosystems, Foster City, Calif.).

Example 2

ATL1102 Mobilizes AML Cells into the Peripheral Blood of NOD/SCID I12R gamma −/− Mice and Downregulated Integrin α4

ATL1102 can mobilize AML cells in a xenograft model of human HL60 cells after 24 hours of i.v. administration to the peripheral blood (FIG. 1). HL-60 cells (AML; $5 \times 10^6$/per mouse) were injected via the tail vein in sublethally irradiated NSG females mice. Presence of human cells (hCD45) was determined weekly by flow cytometry of white blood cells isolated from peripheral blood. 23 Days post-leukemia injection, mice are randomly split in 3 groups treated with either antisense control (CTRL) (150 mg/kg, n=3), ATL1102 (50 mg/kg, n=4) or ATL1102 (150 mg/kg, n=3). Peripheral blood was drawn before and 2 and 24 hours after ATL-1102-treatment and white blood cells isolated and stained for murine (m) CD45, human (h) CD45 and hCD33. ATL1102 induced a strong mobilization of AML cells to the peripheral blood of leukemia-recipient mice compared to control antisense treated-mice (52.8%±45.4% vs 9.8%±15.9% at 24 h after treatment using 50 mg/kg ATL1102, n=3).

The number of CD49d positive cells and the PE mean of fluorescence were measured. The mobilized cells showed a marked decrease of surface expression of CD49d (16.8%±9.2% vs 32.8%±16.7%, n=3). The microenvironment in vivo may allow uptake of ATL1102 in AML cells.

In some embodiments, AML cells are mobilized from the bone marrow. After 33 hours, AML cells in the peripheral blood are decreased. In some embodiments, this is due to decreased viability or proliferative capacity.

Example 3

In Vitro CD49d Expression in HL-60 Cells: ATL1102 Downregulates CD49d

Figure 2A:
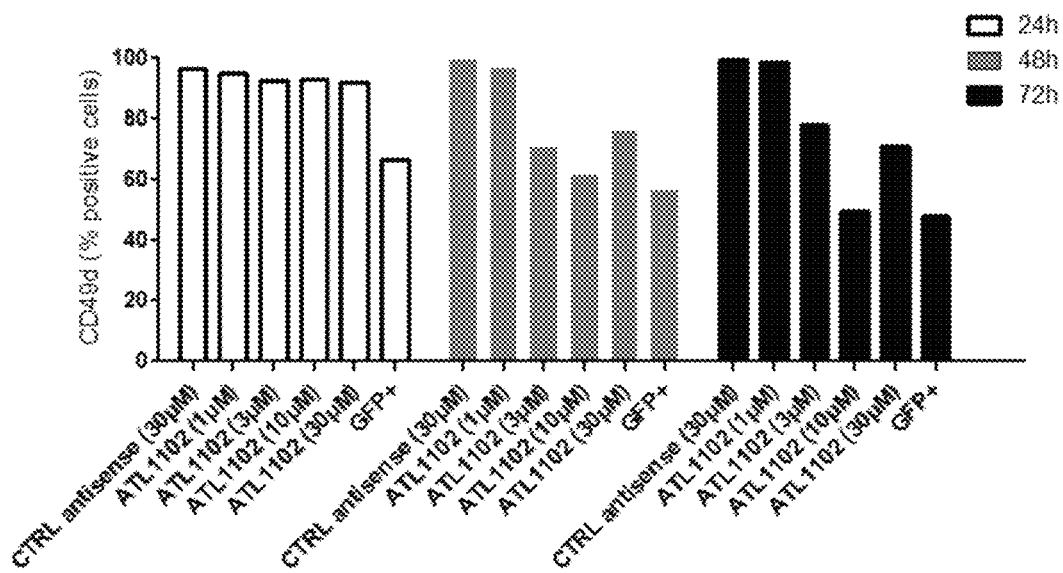
FIGS. 2A and 2B. ATL1102 downregulates CD49d in vitro. CD49d expression was determined by flow cytometry after 24, 48 and 72 hours of nucleoporation of HL60 cells with ATL1102 (1, 3 and 10 μM) or scrambled control (30 μM).
Figure 2B:
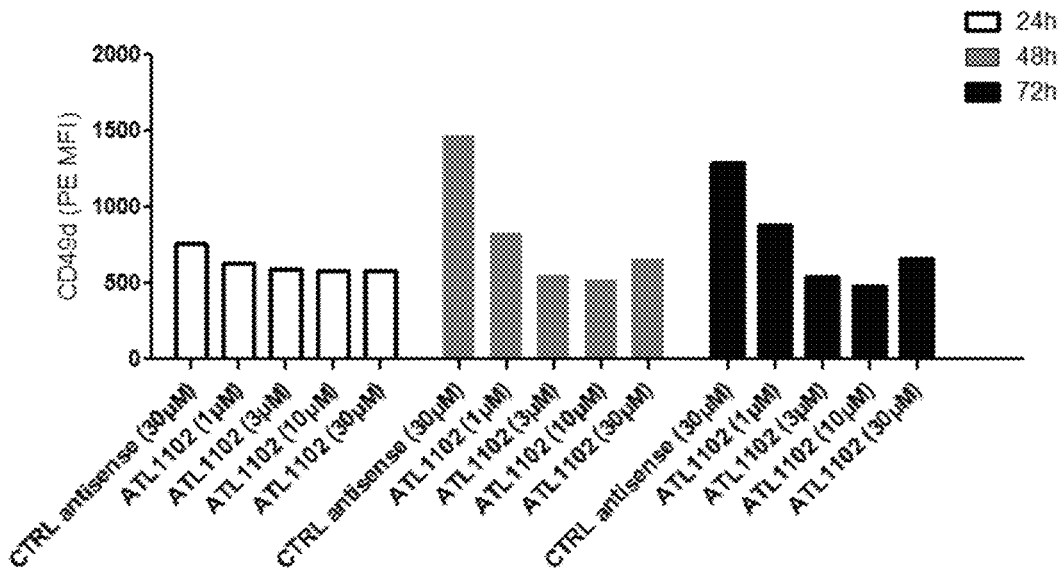
Figure 3A:
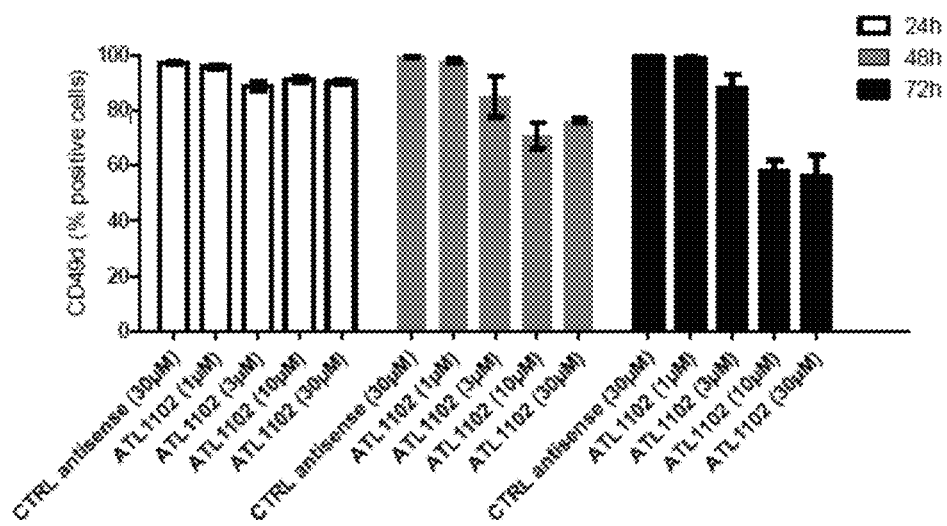
FIGS. 3A-D. Effect of ATL1102 on AML HL-60 cell line. HL-60 cells ($3 \times 10^6$) were nucleofected with a control antisense (30 μM) or ATL1102 (1 μM, 3 μM, 10 μM and 30 μM) using Amaxa Nucleofector Kit V (Lonza).
Figure 3B:
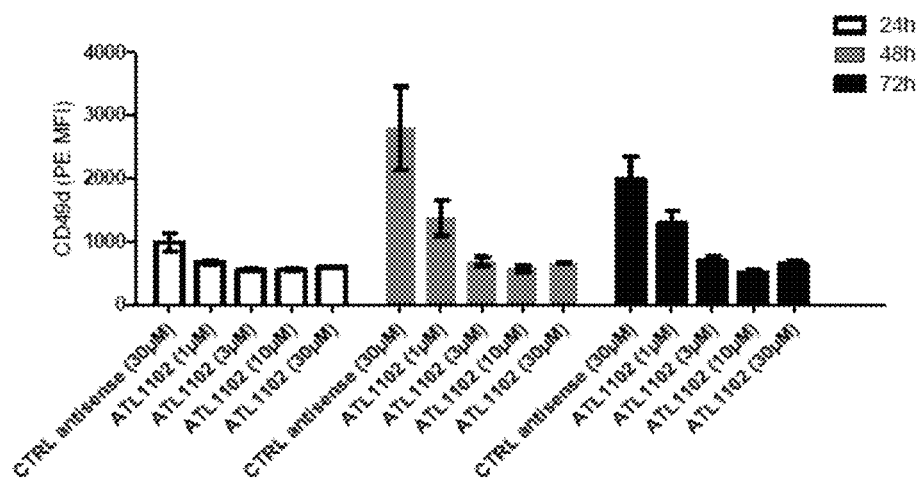
Figure 3C:
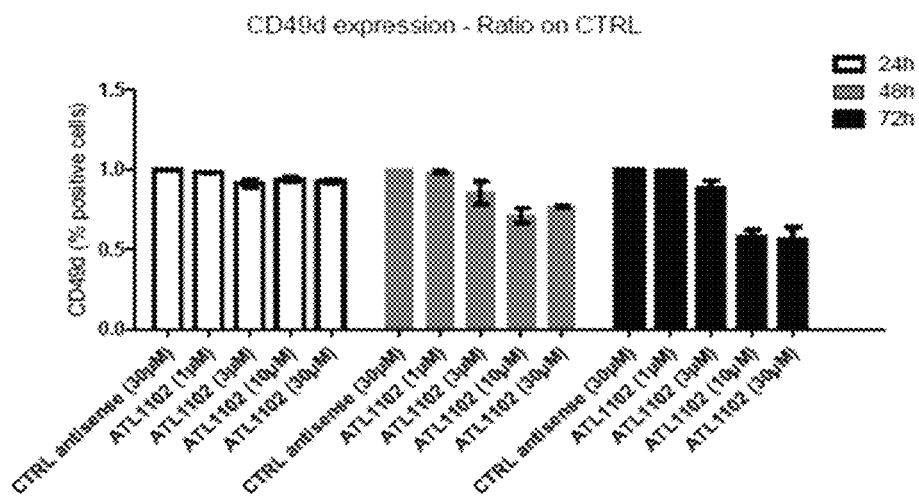
Figure 3D:
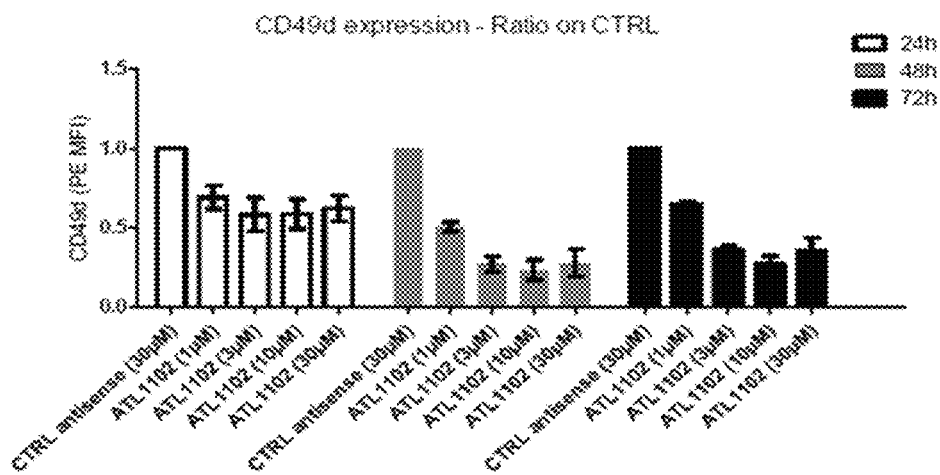

In vitro effects with ATL1102 can be observed after nucleoporation of AML cells. CD49d expression was determined by flow cytometry after 24, 48 and 72 hours of nucleoporation of HL60 cells with ATL1102 (1, 3 and 10 μM) or scrambled control (30 μM). CD49d is markedly downregulated compared with scrambled control after 48 hours and 72 hours in a dose-dependent way (FIG. 2). GFP+ cells were included as control (were not stained for CD49d). Mean fluorescence intensity is also affected. HL-60 cells ($3 \times 10^6$) were nucleofected with a control antisense (30 μM) or ATL1102 (1 μM, 3 μM, 10 μM and 30 μM) using Amaxa Nucleofector Kit V (Lonza). (A) The CD49d expression is assessed by flow cytometry every 24 hours after treatment for 72 hours. (B) The number of CD49d positive cells and the PE mean of fluorescence are measured. (C) Ratio of CD49d expression compared to Ctrl. (D) Ratio of the mean of fluorescence of CD49d positive cells compared to Ctrl. The FACS analysis revealed a significant decrease of surface expression of CD49d in a dose-dependent manner (57.8%±7.2 ATL1102 (10 μM) vs 99.7%±0.1 for control antisense (30 μM), P<0.001, n=3, 72 h after ATL1102 treatment). CD49d expression on mRNA level was significantly decreased by integrin α4 antisense ATL1102 treatment in HL-60 human AML cell line (85.2%±15.4 expression inhibition using ATL1102 1 μM after 24 h compared to control, p<0.001) as assessed by RT-PCR. See FIG. 3.

Example 4

In Vitro Apoptosis Assay in Nucleofected HL-60 Cells. Effect of ATL1102

Figure 4:
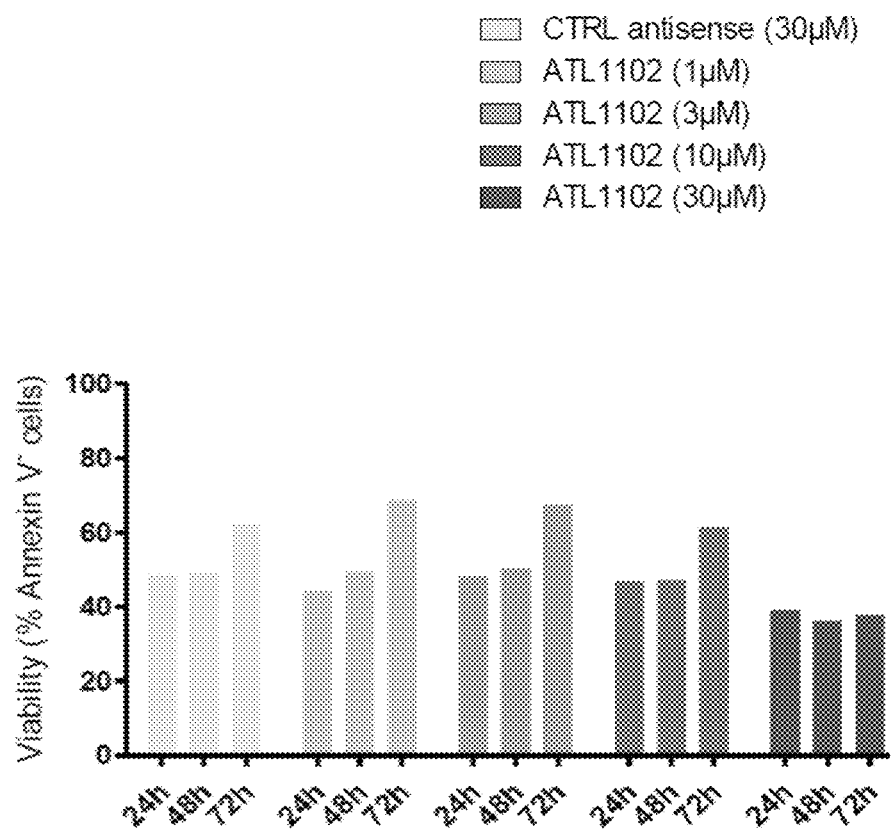
FIG. 4. Effect of ATL1102 on AML HL-60 cell line. HL-60 cells were nucleofected with a control antisense (30 μM) or ATL1102 (1 μM, 3 μM, 10 μM and 30 μM) using Amaxa Nucleofector Kit V (Lonza). Apoptosis assay was performed using double staining AnnexinV (PE)/DAPI and assessed by flow cytometry every 24 hours after treatment for 72 hours. Effect on apoptosis of HL60 cells was observed after ATL1102 treatment at above 10 μM.

HL-60 cells were nucleofected with a control antisense (30 μM) or ATL1102 (1 μM, 3 μM, 10 μM and 30 μM) using Amaxa Nucleofector Kit V (Lonza). Apoptosis assay was performed using double staining AnnexinV (PE)/DAPI and assessed by flow cytometry every 24 hours after treatment for 72 hours. An effect on apoptosis of HL60 cells was observed after higher doses of ATL1102 treatment. See FIG. 4.

Example 5

In Vitro Cell Cycle Assay in Nucleofected HL-60 Cells. Effect of ATL1102

Figure 5A:
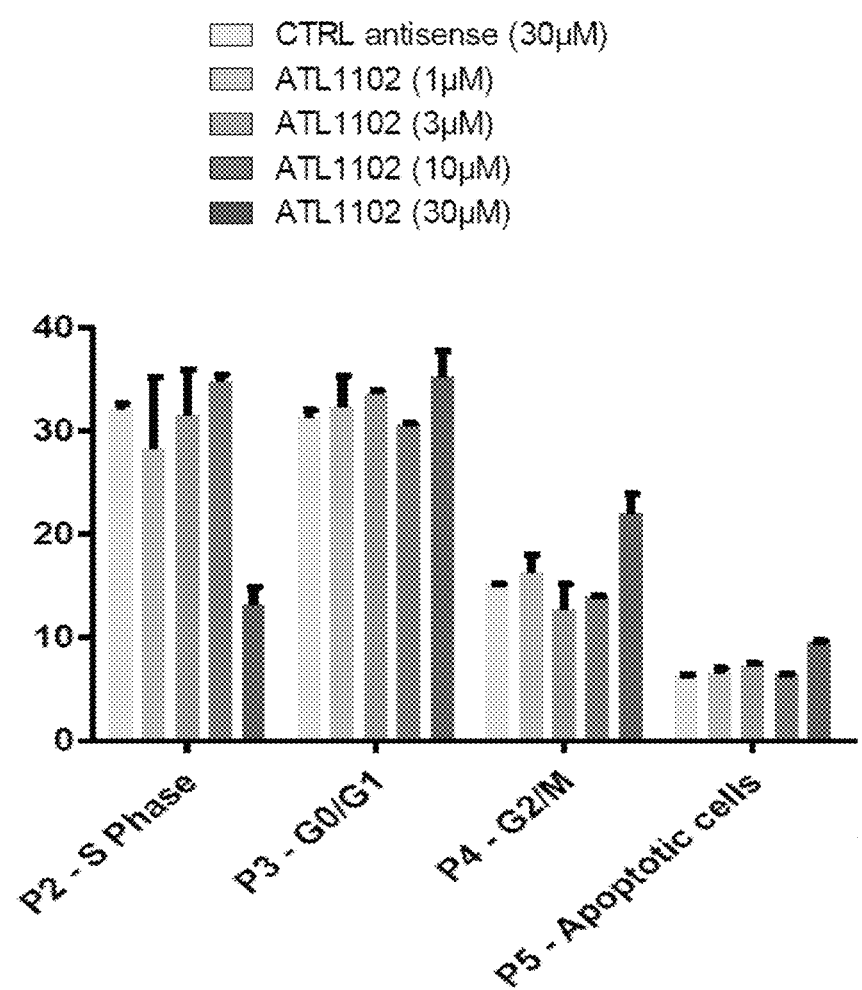
FIGS. 5A and 5B. Effect of ATL1102 on AML HL-60 cell line. HL-60 cells (($3 \times 10^6$) were nucleofected with a control antisense (30 μM) or ATL1102 (1 μM, 3 μM, 10 μM and 30 μM) using Amaxa Nucleofector Kit V (Lonza).
Figure 5B:
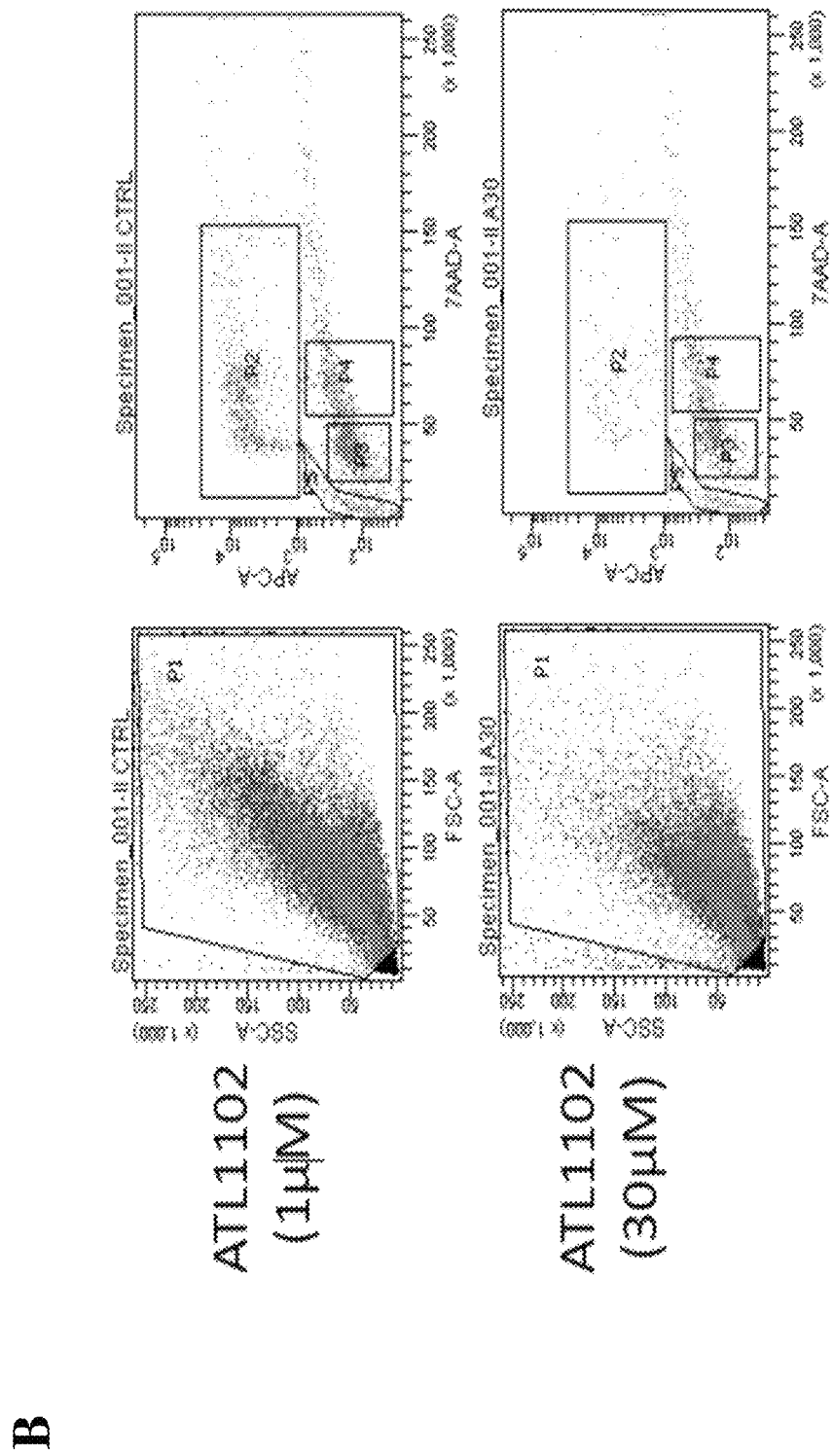

HL-60 cells (($3 \times 10^6$) were nucleofected with a control antisense (30 μM) or ATL1102 (1 μM, 3 μM, 10 μM and 30 μM) using Amaxa Nucleofector Kit V (Lonza). (A) The effect of ATL1102 was assessed by BrdU/7-AAD staining and revealed by flow cytometry at 48 hours after treatment. (B) Examples of the flow cytometric gates used for cell cycle analysis is shown for 1 μM and 30 μM ATL1102. Some effect on cell cycle of HL60 cells was observed after higher doses of ATL1102 treatment. See FIG. 5.

Example 6

Design of Mobilization Assay

Figure 6:
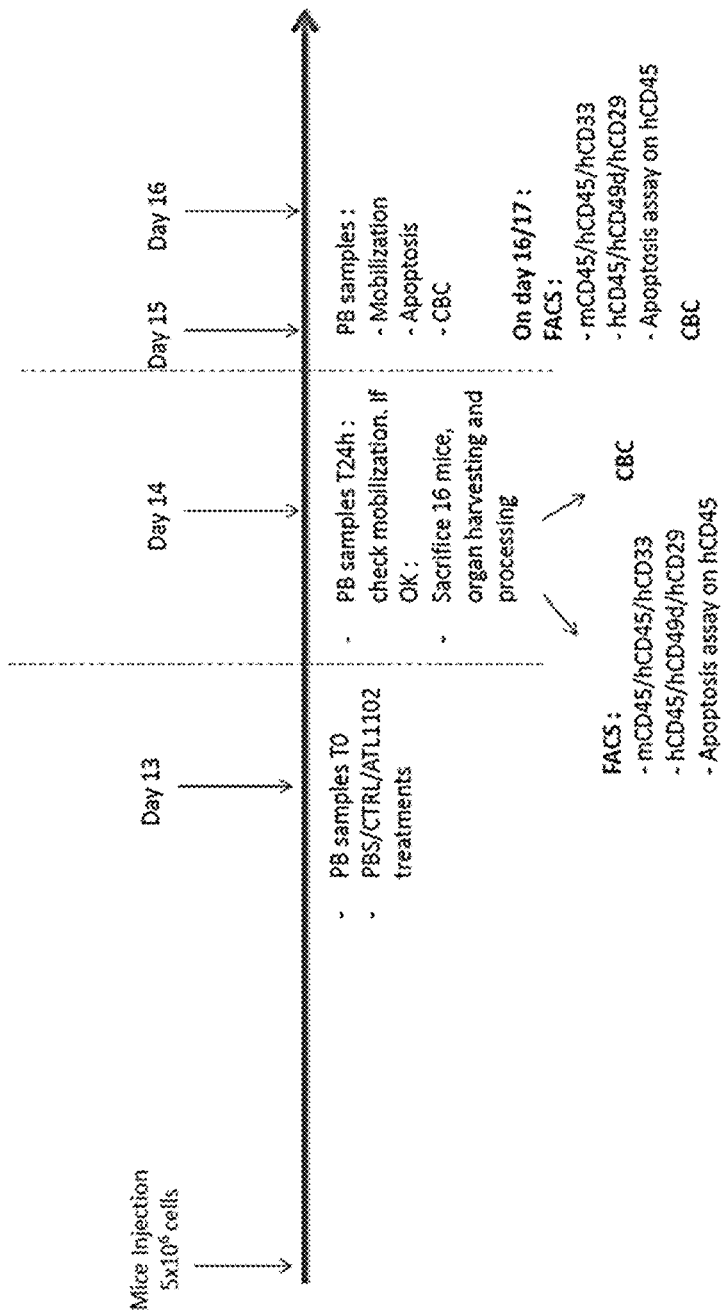

HL-60 cells ($5 \times 10^6$/per mouse) were injected via the tail vein in sublethally irradiated NSG mice. Presence of human cells (hCD45) was determined weekly by flow cytometry of white blood cells isolated from peripheral blood (PB). 23 Days post-leukemia injection, mice were treated with either antisense control (CTRL) (150 mg/kg, n=3), or ATL1102 (50 mg/kg, n=4). PB was drawn before and 24 hours after ATL1102-treatment. Mice to be sampled on Day 0 and treated with ATL1102 or control 24 hours later. Peripheral blood to be assayed for mobilization of mCD45/hCD45/hCD33 cells by flow cytometry. If mobilized, most of the mice are sacrificed (the first 4 groups) and organs harvested (peripheral blood, spleen and bone marrow). All the mice will be stained for an engraftment study (mCD45/hCD45/hCD33), for hCD49d and hCD29 expression and for an apoptosis (Annexin V/7AAD) and cell numbers (by Tryanblue exclusion of dead cells) will be counted with the goal to determine if the mobilized cells go back to the bone marrow, move to another organ or die in the blood (especially in the "long term" experiment). A complete blood count will also be performed using a Hemavat5/Hemanalyzer See FIG. 6.

Example 7

Transduction of HL-60 with Luciferase Expressing Vector

Figure 7A:
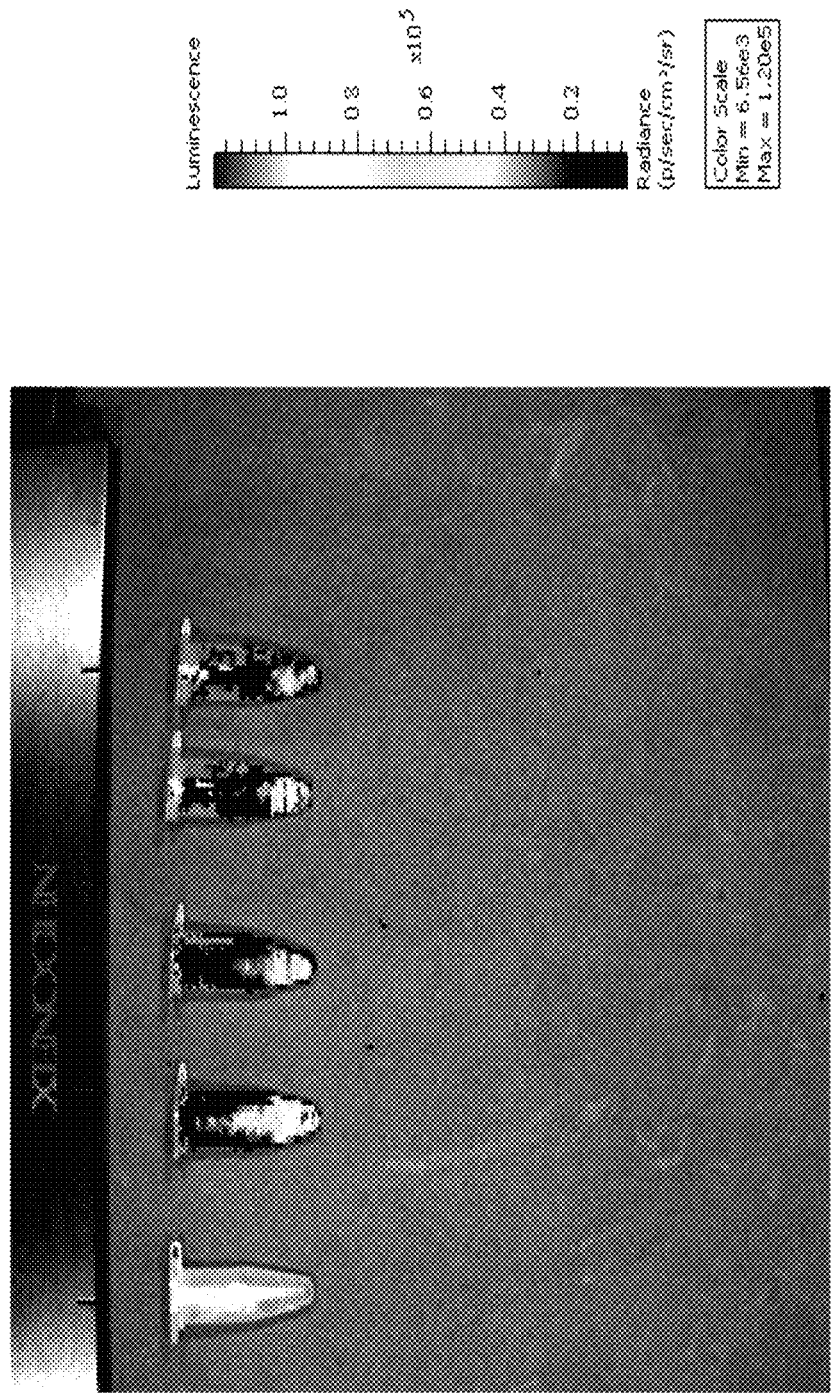
FIGS. 7A and 7B Transduction of HL-60 with luciferase expressing vector. HL 60 cells were transduced with lentiviral firefly luciferase, (Hsieh et al. *Blood* 121 (10):1814-1818, 2013).
Figure 7B:
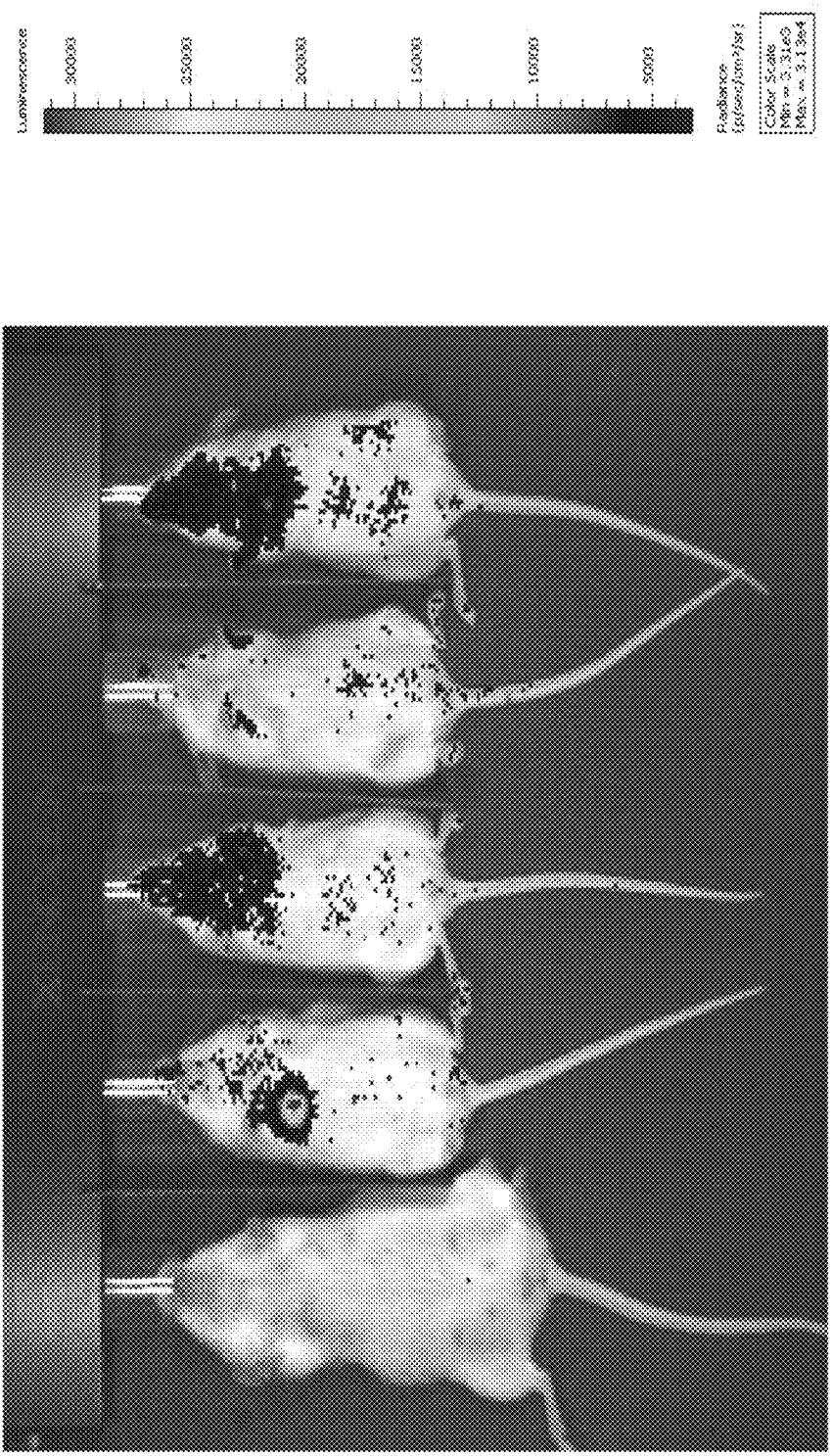

HL 60 cells were transduced with lentiviral firefly luciferase, (Hsieh et al. Blood 121 (10):1814-1818, 2013). See FIG. 7.

Example 8

Results

ATL1102 can efficiently decrease CD49d expression in AML cell line in vitro and in vivo, and ATL1102 leads to mobilization of AML cells to the peripheral blood.

HL-60 cells were nucleoporated with either ATL1102 or control antisense. mRNA expression of CD49d was significantly decreased by ATL1102 treatment cells (85.2%±15.4 expression inhibition using ATL1102 1 µM after 24 h compared to control, p<0.001) as assessed by RT-PCR. The FACS analysis 72 hours after treatment revealed a significant decrease of surface expression of CD49d in a dose-dependent manner (99%±0.4 (1 µM, *), 87.9%±8.7 (3 µM) and 57.8%±7.2 ATL1102 (10 µM, *), 55.9±13.5 (30 µM, ) vs 99.7%±0.1 for control antisense (30 µM), P<0.001, n=3). No significant effect on apoptosis or cell cycle was observed after ATL1102 treatment although effects on apoptosis was observed at above 10 µM.

The in vivo effect of ATL-1102 on mobilization of leukemia cells was evaluated in a pilot experiment. For this purpose, HL-60 cells (5×10⁶/per mouse) were injected via the tail vein in sublethally irradiated NSG mice. Presence of human ALL cells (hCD45) was determined weekly by flow cytometry of white blood cells isolated from peripheral blood (PB). 23 Days post-leukemia injection, mice were treated with either antisense control (CTRL) (n=3), ATL1102 (50 mg/kg, n=2). Peripheral blood was drawn before and 24 hours after ATL1102-treatment. ATL1102 induced a strong mobilization of AML cells to the PB of leukemia-recipient mice compared to control antisense treated-mice (69.1% and 87.7% vs 1.1%, 0.2% and 28.1% for ATL1102 (50 mg/ml) and CTRL treated-mice respectively. The mobilized cells show a decrease of surface expression of CD49d (16.8%±9.2% vs 32.8%±16.7%).

Example 8

Combination of ATL1102 and Ara-C Reduces AML Cancer Load In Vivo and Prolongs Survival Compared to Ara-C Treatment Alone Ara-C(Cytarabine) is the chemotherapy medication most often used in induction therapy to treat acute myeloid leukemia, ALL, CML and non-Hodgkin's lymphoma. The human myeloid cell, U937 was used which is a monocyte-like, histiocytic-monocyte leukemia cell. NSG female mice were engrafted with 5×10⁴ U937 cells transfected with an illuminescence luciferase marker. This compares with HL60 AML cells which represent a subset of leukemia cells which as neutrophilic promyelotic cells.

Four groups of six mice were dosed with Ara-C, ATL1102, control ASO or combinations of ATL1102 and Ara-C. The ATL1102 and control mice were dosed on days 3 (week 1), 11 (week 2), 18, 20 and 22 (week 3) and day 25 (week 4) and did not survive to receive the scheduled day 27 and 31 doses in week 4. All these mice had died by day 27. The Ara-C was administered 3 times per week for 4 weeks (days 3, 5 and 7 in week 1, days 11, 13, 15 in week 2, days 18, 20, 22 in week 3, and days 25, 27 and 31 in week 4. The last Ara-C treated mouse died on day 45. In the ATL1102 and Ara-C combination treatment, mice were dosed Ara-C 3 times per week for 4 weeks as described above and also received ATL1102 on all the above scheduled doses to day 31 (week 4) (See FIG. 8A). In the combination group all mice were still alive after day 40 and the last mouse died on day 53. Ara-C was administered at 100 mg/kg 3 times per week for the first 5 administrations and at 300 mg/kg thereafter. ATL1102 or control ASO were administered at 150 mg/kg/time, once per week for the first 2 weeks followed by a scheduled 3 times per week as described above.

Figure 8B:
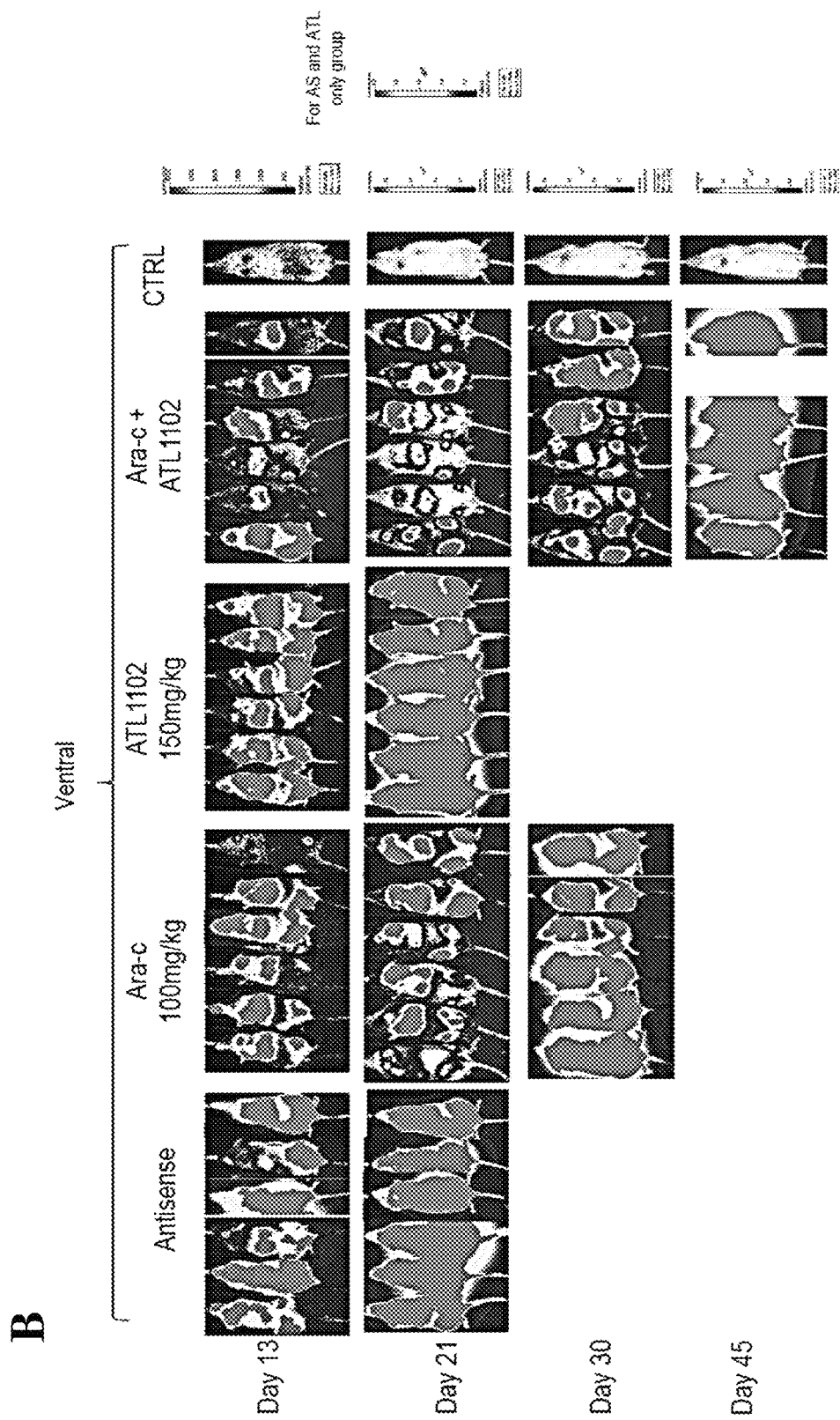
Figure 8C:
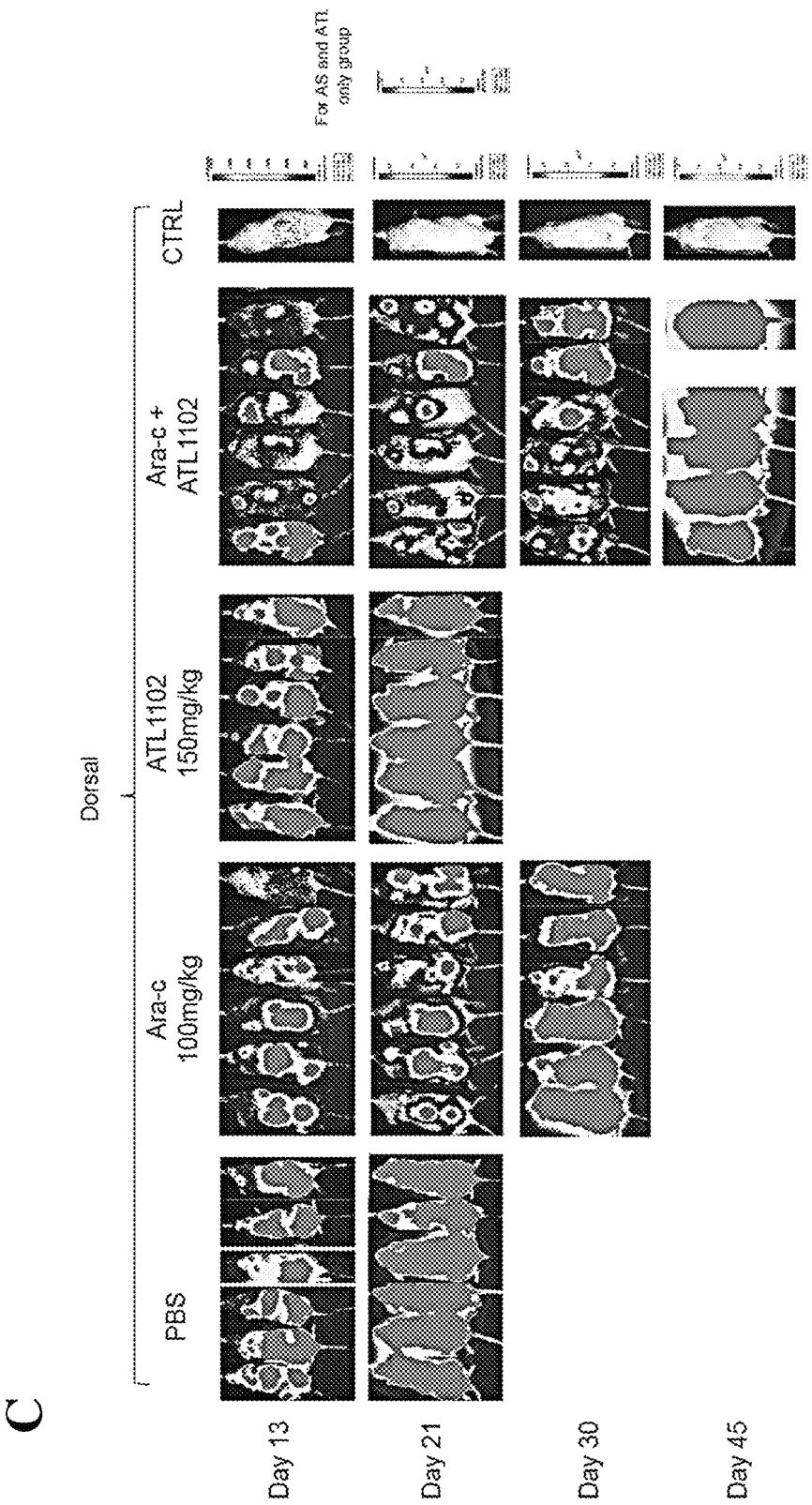

FIG. 8B shows the radiance (illumination) imaging data from the ventral-abdominal side and FIG. 8C shows the radiance from the dorsal-back side. The data shows the distribution of myeloid cells in the mice at different time points. The mice display a wide distribution of bioilluminescence (AML cells) on day 13 in the ATL1102 and antisense control group on day 13 and more on day 21 with significantly less illuminescence in the Ara-C group and even less illuminescence in the combination treatment group. By day 21 there was a statistically significant (p=0.038) 61% reduction in illuminescence in the dorsal side in the combination group vs Ara-C alone and a trend 69% reduction in the ventral side (p=0.056)). Illumination increased 2.55 and 2.92 fold from day 21 to 30 in the dorsal and ventral sides respectively in the combination, and 7.3× and 5.9× i.e. 2 to 3 fold more in the monotherapy.

Figure 9:
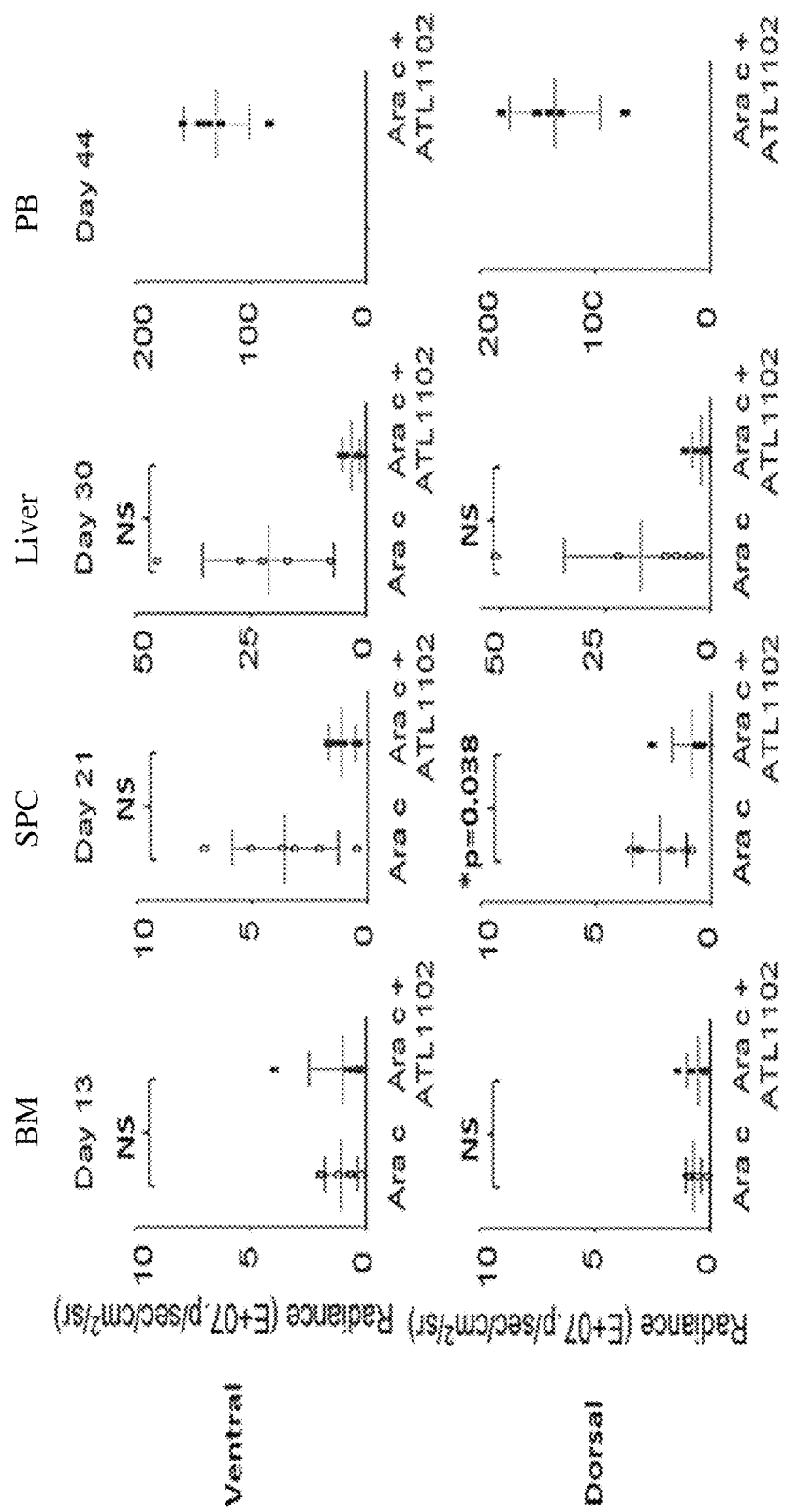
FIG. 9 graphically illustrates the FACS data on the percentage of hCD49d expressing CD45+ AML cells and respective mean fluorescence intensity (MFI) and the percentage of hCD49 expression on AML cells in mice undergoing Ara-C monotherapy (day 43) and Ara-C and ATL1102 combination therapy (day 44) in the bone marrow (BM), spleen (SPC), liver and peripheral blood (PB).

The results of quantifying the bioimage signal at the various time points as shown in FIG. 8, and statistical analysis, is represented in FIG. 9.

Figure 10A:
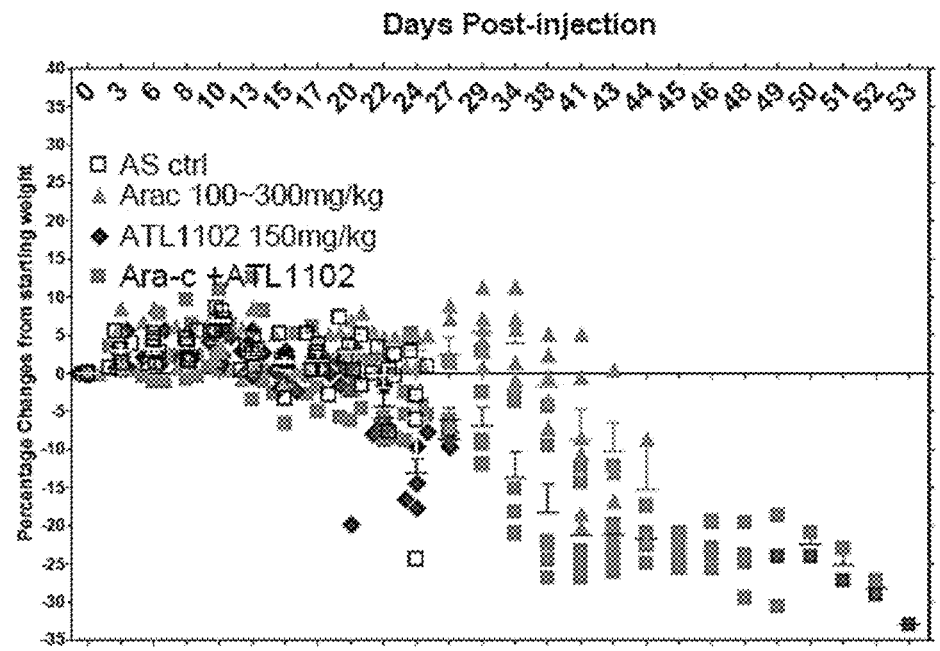
FIG. 10A is a graphical representation of data showing the percent change in mouse weight from the starting weight in all the treatment groups over the full course of the experiments.
Figure 10B:
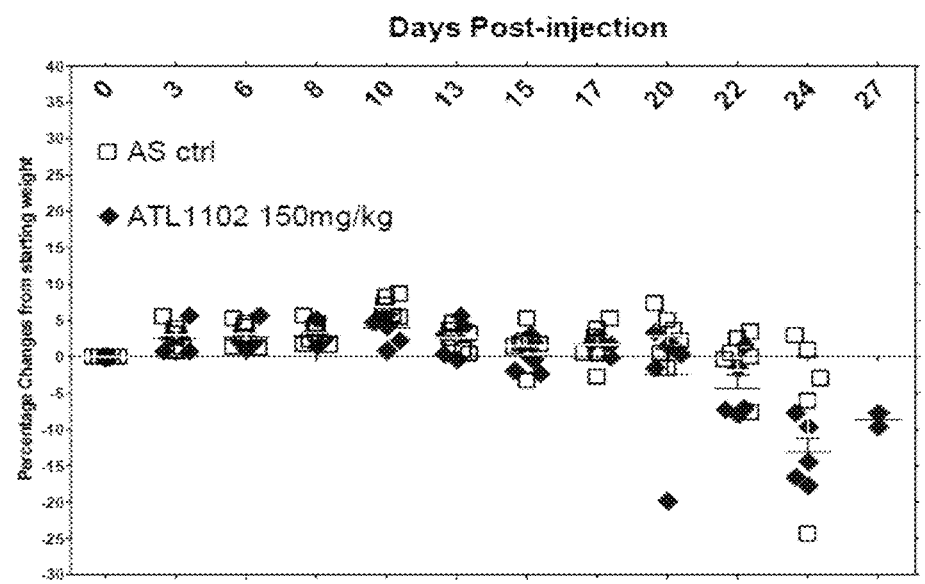
FIG. 10B is a graphical representation of data showing the percent change in mouse weight from the starting weight in the control antisense (AS) and ATL1102 treatment group to day 27.

FIG. 10A is a graphical representation of data showing the percent change in mouse weight from the starting weight in all the treatment groups over the full course of the experiments. FIG. 10B is a graphical representation of data showing the percent change in mouse weight from the starting weight in the control antisense (AS) and ATL1102 treatment group to day 27.

Figure 11:
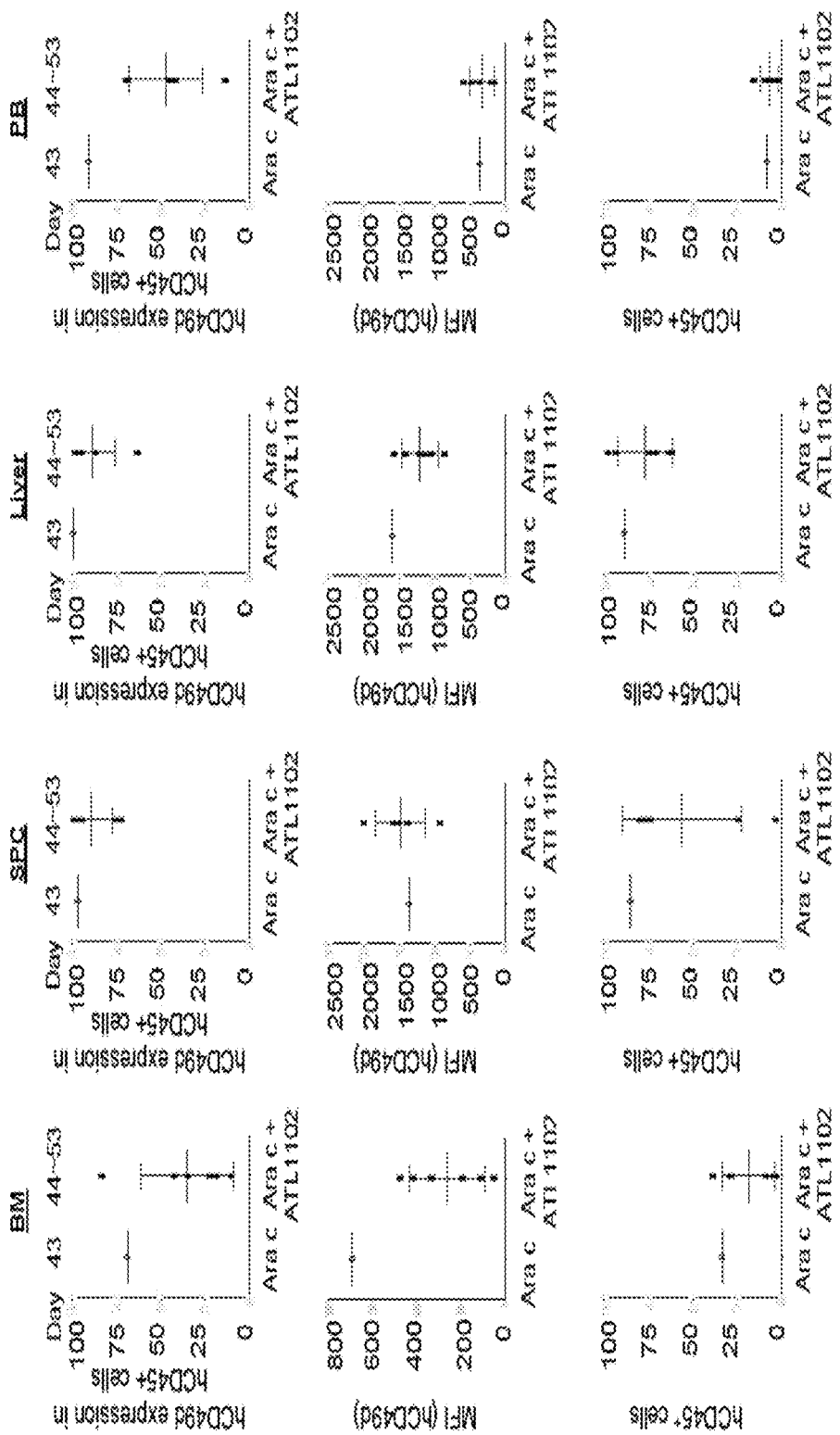
FIG. 11 is a graphical representation of FACs data showing the percentage of hCD49d expressing AML cells (top row), the level of hCD49d expression by mean fluorescence intensity (middle row) and the percentage of hCD45$^+$ cells (bottom row) in mice undergoing Ara-C monotherapy (day 43) and Ara-C and ATL1102 combination therapy (day 44-53), in the bone marrow (BM), Spleen (SPC), liver and peripheral blood (PB).

FIG. 11 is a graphical representation of FACs data showing the percentage of hCD49d expressing AML cells (top row), the level of hCD49d expression by mean fluorescence intensity (middle row) and the percentage of hCD45⁺ cells (bottom row) in mice undergoing Ara-C monotherapy (day 43) and Ara-C and ATL1102 combination therapy (day 44), in the bone marrow (BM), Spleen (SPC), liver and peripheral blood (PB).

In the bone marrow (BM—FIG. 11 left hand column) there are fewer human (hCD49d+) AML cells in the ATL1102 and Ara-C combination compared to the Ara-C monotherapy (i.e. 70% vs 30%). This suggests they have been released from the bone marrow or do not survive in the bone marrow because of ATL1102 treatment, consistent with mobilization of these cells from the bone marrow/or apoptosis of these AML cells (see also FIG. 13). Thus in some embodiments, the ATL1102 treatment sensitizes the AML cells to clearance by Ara-C. The cells that were still in the bone marrow expressed substantially less hCD49d (i.e., 800 vs about 450 MFI) suggesting good CD49d target knockdown. This was more pronounced in the peripheral blood (PB). In the spleen there is no difference in % of human AML cells, but the cells in the spleen appear to express more hCD49d. In the liver there are no differences in either % or MFI.

Figure 12A:
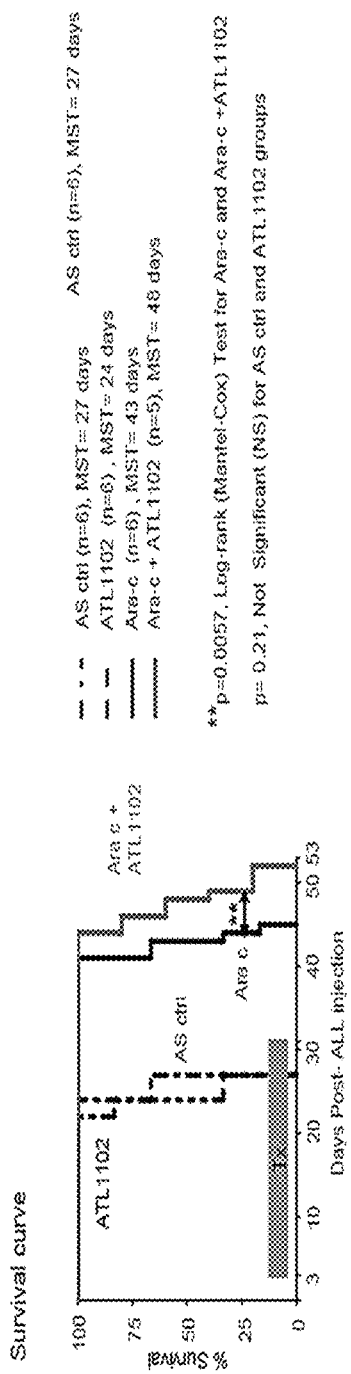
FIGS. 12A-C illustrate the survival of the different treatment/control groups as the data became available. In each graph, there was a statistically significant increase in the survival of the combination treatment group compared to Ara-C treatment alone. Overall, there was a significant 12.8% increase in the median survival in the combination group relative to the monotherapy.
Figure 12B:
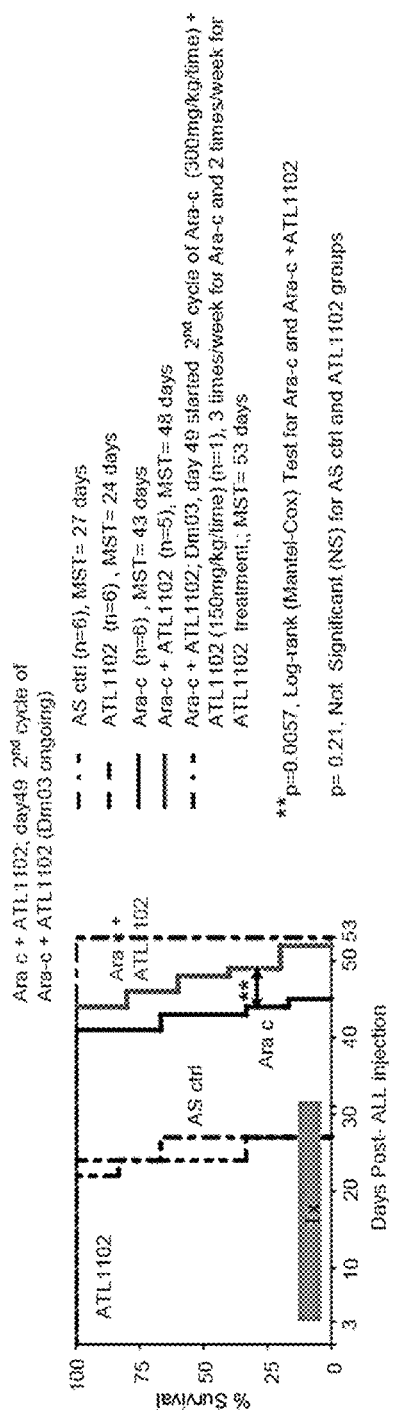
Figure 12C:
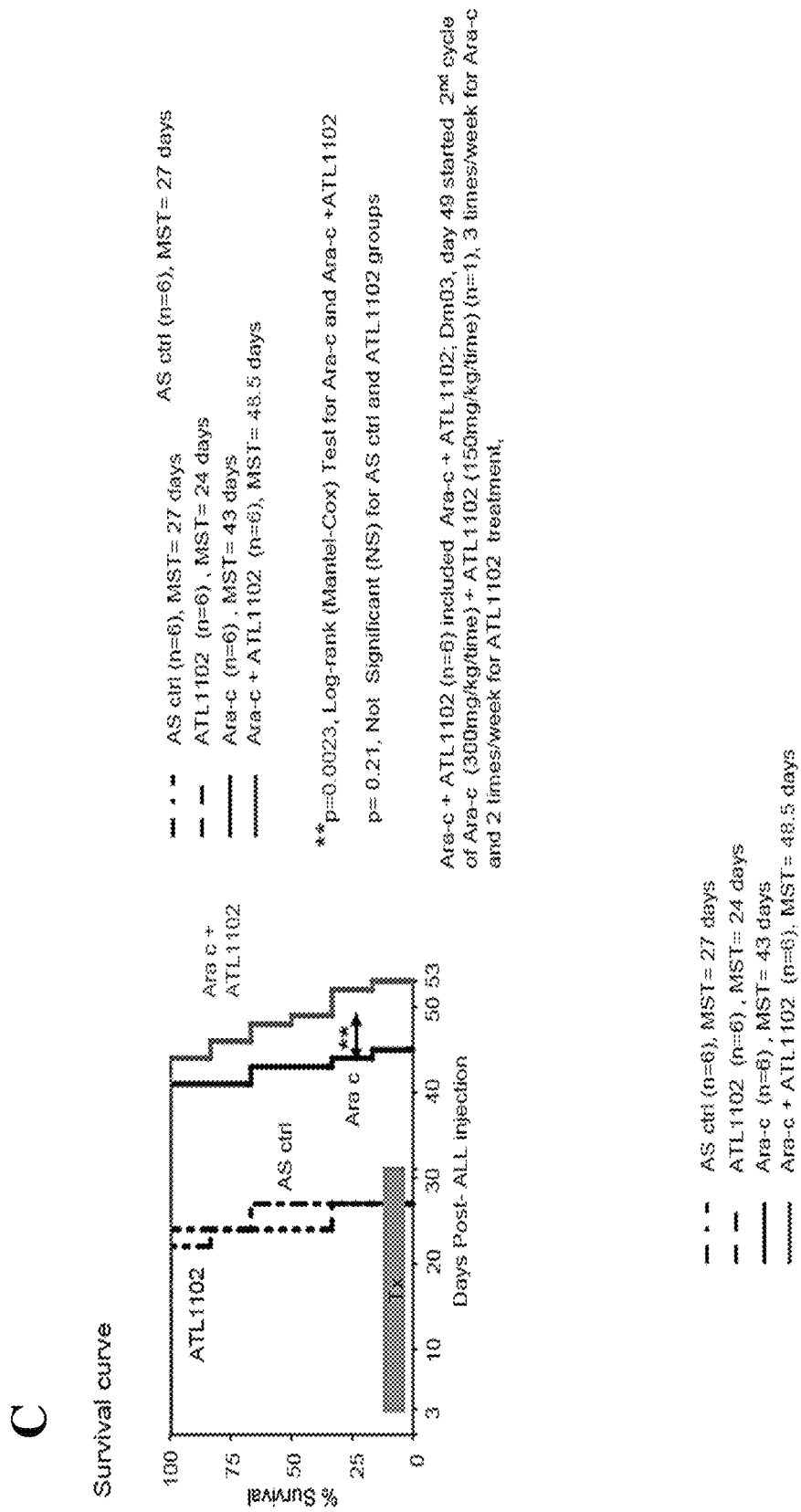

FIG. 12A-C illustrate the survival of the different groups as the data became available. In each graph, there was a statistically significant increase in the survival of the combination treatment group compared to Ara-C treatment alone. Overall, there was a significant 12.8% increase in the median survival in the combination group relative to the monotherapy.

Figure 13A:
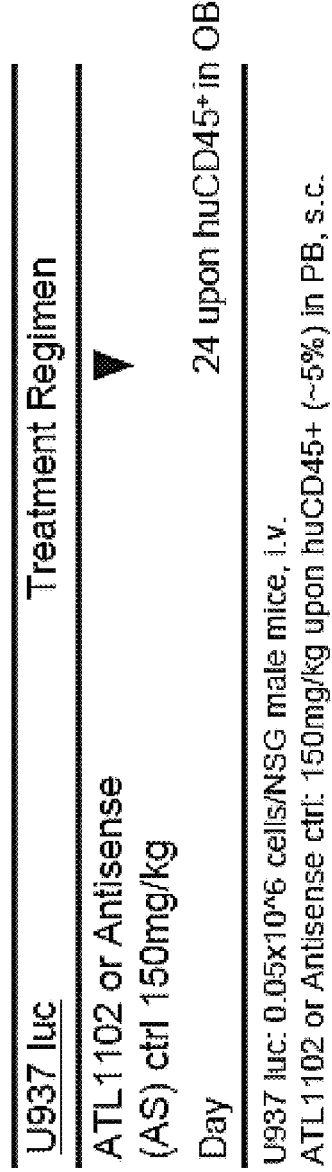
FIGS. 13A-B graphically illustrate the results of an experiment to evaluate mobilization of engrafted human AML cells (expressing hCD45) in tissues over 24 hours after ATL1102 administration.
Figure 13B:
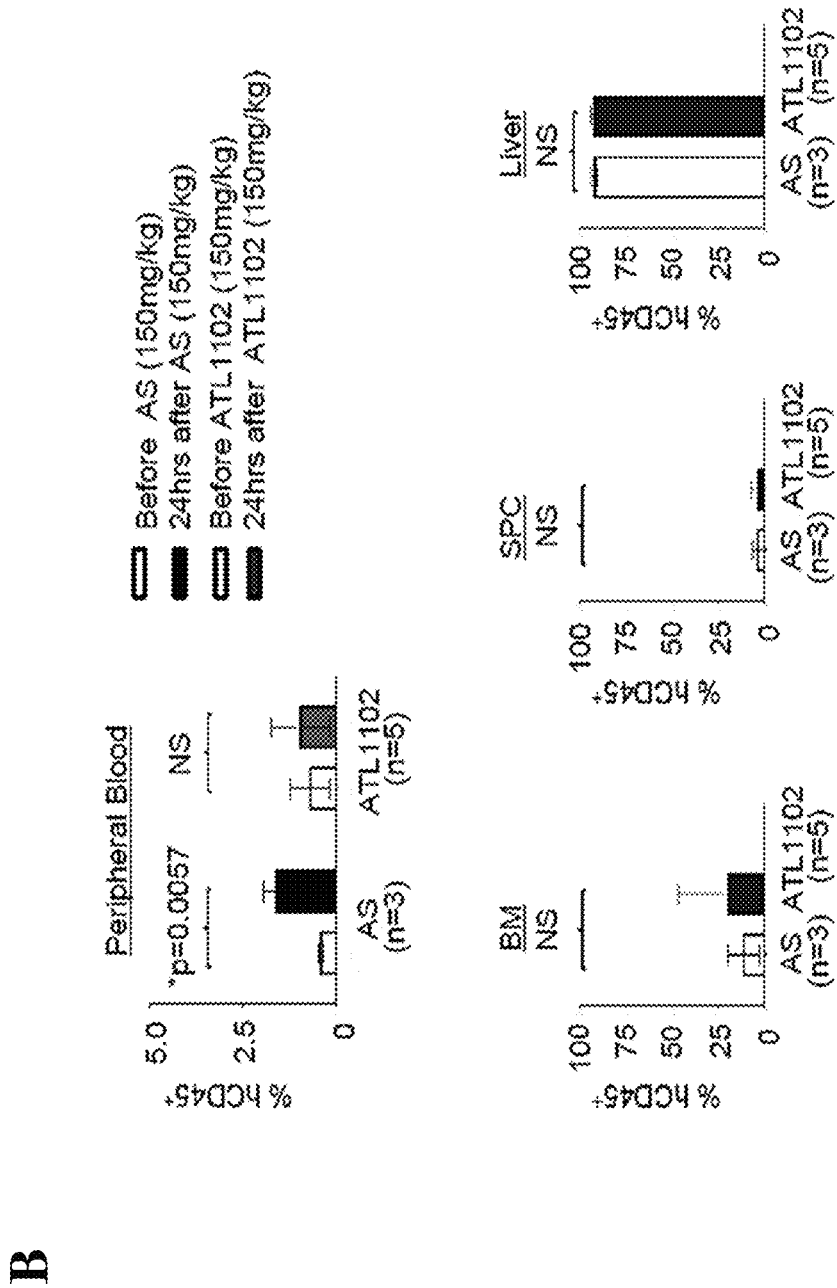

An experiment was also conducted to evaluate mobilization of engrafted human U937 AML cells (expressing hCD45) in tissues over 24 hours after ATL1102 and AS control administration in male NSG mice on day 24 after engraftment. As shown in FIG. 13, bone marrow has 10-25% human CD45+/AML cells (i.e. vs 75-90% mouse CD45+ leukocytes), the liver has over 90% human CD45+/AML cells, and in the spleen <5% with no significant differences in AS control vs ATL1102 mice at baseline or 24 hours post 150 mg/kg dose. There is, however, with the control AS a significant increase in AML cells in PB at 24 hours vs baseline to ~2% AML. In contrast there is only 1% AML cells in peripheral blood treated at 24 hours with compared to ATL1102 treated animals, and no significant increases vs baseline. AML cells could be expected to move from tissues to the PB within 24 hours of dosing as occurs with control AS. In the control there was a statistically significant increase in the % of AML cells in the peripheral blood at day 4 vs baseline, but not in the ATL1102 treated group. This indicates U937 cells treated with ATL1102 show reduced survival in the blood.

It will be appreciated by persons skilled in the art that numerous variations and/or modifications may be made to the above-described embodiments, without departing from the broad general scope of the present disclosure.

REFERENCES

Altschul et al., J. Mol. Biol. (1990) 215:403-410
Camos et al., Clin. Transl. Oncol. 8 (8):550-9, 2006
Döhner et al., New England Journal of Medicine 15 2015 Sep. 17; 373(12):1136-52
Elbashir et al., Nature (2001a) 411:494-498
Elbashir et al., Genes Dev. (2001b) 15:188-200
Englisch et al., Angewandte Chemie, International Edition (1991) 30:613
Fire et al., Nature (1998) 391:806-811
Gaynon et al. Cancer 1998; 82:1387-1395
Guo and Kempheus, Cell (1995) 81:611-620
Hsieh et al. Blood 2013; 121:1814-1818
Hunger et al., New England Journal of Medicine 15; 373 (16):1541-52, 2015
Matsunaga et al. Nature Medicine 2003; 9:1158-1165
Montgomery et al., Proc. Natl. Acad. Sci. USA. (1998) 95:15502-15507
Nielsen et al., Science (1991) 254, 1497-1500
Park et al. Blood (2011) 118:2191-2199
Schlenk et al. N. Engl. J. Med. 2008; 358:1909-1918
Tabara et al., Science (1998) 282:430-431
Tijsterman et al., Science (2002) 295:694-697
Timmons and Fire, Nature (1998) 395:854
Tuschl et al., Genes Dev. (1999) 13:3191-3197
Zhang and Madden, Genome Res. (1997) 7:649-656
Wunderlich et al. Blood (2013) 121:e90-e97.

The invention claimed is:

1. A method for mobilizing Acute Myeloid Leukemia (AML) cells which are α4 integrin positive to the peripheral blood of a human subject, the method comprising administering to the human subject having AML an effective amount of an antisense oligonucleotide to α4 integrin wherein the antisense compound is fully complementary over the entirety of said oligonucleotide to a nucleic acid encoding human α4 integrin, wherein the oligonucleotide consists of a deoxynucleotide region flanked on both of the 5' and 3' ends with one or more 2'-O-modified sugar moieties, and wherein the oligonucleotide comprises at least one 2'-O-methoxyethyl sugar moiety, at least one phosphorothioate internucleoside linkage, and at least one 5-methylcytosine.

2. The method of claim 1, wherein the AML cells are mobilized from the bone marrow.

3. The method of claim 1, wherein the antisense compound is:

$$5'\text{-}^{Me}C^{Me}\text{UG AGT }^{Me}\text{CTG TTT }^{Me}U^{Me}C^{Me}C\ A^{Me}U^{Me}U\ ^{Me}C^{Me}U\text{-}3' \quad (\text{SEQ ID NO: 1})$$

wherein,
a) each of the 19 internucleotide linkages of the oligonucleotide is an O,O-linked phosphorothioate diester;
b) the nucleotides at the positions 1 to 3 from the 5' end are 2'-O-(2-methoxyethyl) modified ribonucleosides;
c) the nucleotides at the positions 4 to 12 from the 5' end are 2'-deoxyribonucleosides;

d) the nucleotides at the positions 13 to 20 from the 5' end are 2'-O-(2-methoxyethyl) modified ribonucleosides; and e) all cytosines are 5-methylcytosines ($^{Me}$C), or a pharmaceutically acceptable salt thereof.

4. The method of claim 1, wherein the AML cells are CD123+, CD33+, CD34+ and CD38−.

5. The method of claim 1, further comprising administering a therapeutic agent prior to, subsequently, or concurrently with the antisense compound.

6. The method of claim 5, wherein the therapeutic agent is a chemotherapeutic agent.

7. The method of claim 5, wherein the therapeutic agent is administered at least about 24 hours after administration of the antisense compound.

8. The method of claim 5, further comprising monitoring the number of AML cells in the peripheral blood prior administering the therapeutic agent.

9. The method of claim 8, wherein the AML cells are monitored by flow cytometry.

10. The method of claim 8, wherein the AML cells are monitored for expression of one or more cell surface antigenic determinant, selected from CD123, CD33, CD34 and CD38.

11. A method for the treatment of Acute Myeloid Leukemia (AML) in a human subject, said method comprising administering to the subject having AML an effective amount of an antisense oligonucleotide to α4 integrin wherein the antisense compound is fully complementary over the entirety of said oligonucleotide to a nucleic acid encoding human α4 integrin, wherein the oligonucleotide consists of a deoxynucleotide region flanked on both of the 5' and 3' ends with one or more 2'-O-modified sugar moieties, and wherein the oligonucleotide comprises at least one 2'-O-methoxyethyl sugar moiety, at least one phosphorothioate internucleoside linkage, and at least one 5-methylcytosine.

12. The method of claim 11, wherein said method comprises:

(i) administering to the subject the effective amount of the antisense oligonucleotide to α4 integrin; and (ii) administering to the subject a therapeutic agent prior to, subsequently, or concurrently with the antisense compound.

13. The method of claim 12, wherein the therapeutic agent is a chemotherapeutic agent.

14. The method of claim 12 further comprising monitoring the number of AML cells in the peripheral blood prior to administering the therapeutic agent.

15. The method of claim 6, wherein the therapeutic agent is administered at least about 24 hours after administration of the antisense compound.

16. The method of claim 11, wherein the antisense compound is:

5'-$^{Me}$C$^{Me}$UG AGT $^{Me}$CTG TTT $^{Me}$U$^{Me}$C$^{Me}$C A$^{Me}$U$^{Me}$U $^{Me}$C$^{Me}$U-3' (SEQ ID NO: 1)

wherein, a) each of the 19 internucleotide linkages of the oligonucleotide is an O,O-linked phosphorothioate diester;

b) the nucleotides at the positions 1 to 3 from the 5' end are 2'-O-(2-methoxyethyl) modified ribonucleosides;

c) the nucleotides at the positions 4 to 12 from the 5' end are 2'-deoxyribonucleosides;

d) the nucleotides at the positions 13 to 20 from the 5' end are 2'-O-(2-methoxyethyl) modified ribonucleosides; and (iii) all cytosines are 5-methylcytosines ($^{Me}$C), or a pharmaceutically acceptable salt thereof.

* * * * *

SEQUENCE LISTING

```
<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: antisense oligonucleotide
<220> FEATURE:
<221> NAME/KEY: methylcytosine
<222> LOCATION: (1)..(1)
<220> FEATURE:
<221> NAME/KEY: 2'-O-(2-methoxyethyl) modified ribonucleosides
<222> LOCATION: (1)..(3)
<220> FEATURE:
<221> NAME/KEY: methyluracil
<222> LOCATION: (2)..(2)
<220> FEATURE:
<221> NAME/KEY: 2'deoxyribonucleosides
<222> LOCATION: (4)..(13)
<220> FEATURE:
<221> NAME/KEY: methylcytosine
<222> LOCATION: (7)..(7)
<220> FEATURE:
<221> NAME/KEY: methyluracil
<222> LOCATION: (13)..(13)
<220> FEATURE:
<221> NAME/KEY: methylcytosine
<222> LOCATION: (14)..(14)
<220> FEATURE:
<221> NAME/KEY: 2'-O-(2-methoxyethyl) modified ribonucleosides
<222> LOCATION: (14)..(20)
<220> FEATURE:
```

```
<221> NAME/KEY: methylcytosine
<222> LOCATION: (15)..(15)
<220> FEATURE:
<221> NAME/KEY: methyluracil
<222> LOCATION: (17)..(17)
<220> FEATURE:
<221> NAME/KEY: methyluracil
<222> LOCATION: (18)..(18)
<220> FEATURE:
<221> NAME/KEY: methylcytosine
<222> LOCATION: (19)..(19)
<220> FEATURE:
<221> NAME/KEY: methyluracil
<222> LOCATION: (20)..(20)

<400> SEQUENCE: 1
cugagtctgt ttuccauucu                                            20

<210> SEQ ID NO 2
<211> LENGTH: 20
<212> TYPE: DNA
<213> ORGANISM: Artificial Sequence
<220> FEATURE:
<223> OTHER INFORMATION: antisense oligonucleotide
<220> FEATURE:
<221> NAME/KEY: 2'-O-(2-methoxyethyl) modified ribonucleosides
<222> LOCATION: (1)..(5)
<220> FEATURE:
<221> NAME/KEY: 2'deoxyribonucleosides
<222> LOCATION: (6)..(15)
<220> FEATURE:
<221> NAME/KEY: methylcytosine
<222> LOCATION: (9)..(9)
<220> FEATURE:
<221> NAME/KEY: methylcytosine
<222> LOCATION: (10)..(10)
<220> FEATURE:
<221> NAME/KEY: methylcytosine
<222> LOCATION: (12)..(12)
<220> FEATURE:
<221> NAME/KEY: methylcytosine
<222> LOCATION: (13)..(13)
<220> FEATURE:
<221> NAME/KEY: 2'-O-(2-methoxyethyl) modified ribonucleosides
<222> LOCATION: (16)..(20)
<220> FEATURE:
<221> NAME/KEY: methylcytosine
<222> LOCATION: (18)..(18)
<220> FEATURE:
<221> NAME/KEY: methylcytosine
<222> LOCATION: (19)..(19)
<220> FEATURE:
<221> NAME/KEY: methylcytosine
<222> LOCATION: (20)..(20)

<400> SEQUENCE: 2
atatttttcc acctgtgccc                                            20
```